US010251675B2

(12) United States Patent
Ignon et al.

(10) Patent No.: US 10,251,675 B2
(45) Date of Patent: *Apr. 9, 2019

(54) DEVICES, SYSTEMS AND METHODS FOR TREATING THE SKIN

(71) Applicant: EDGE SYSTEMS LLC, Signal Hill, CA (US)

(72) Inventors: Roger Ignon, Redondo Beach, CA (US); Ed F. Nicolas, Signal Hill, CA (US); Scott R. Mallett, Coto De Caza, CA (US)

(73) Assignee: Edge Systems LLC, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/430,209

(22) Filed: Feb. 10, 2017

(65) Prior Publication Data

US 2017/0245876 A1 Aug. 31, 2017

Related U.S. Application Data

(63) Continuation of application No. 14/211,290, filed on Mar. 14, 2014, now Pat. No. 9,566,088.
(Continued)

(51) Int. Cl.
*A61F 7/00* (2006.01)
*A61N 5/02* (2006.01)
(Continued)

(52) U.S. Cl.
CPC ............ *A61B 17/545* (2013.01); *A61B 50/20* (2016.02); *A61B 50/22* (2016.02); *A61F 7/007* (2013.01);
(Continued)

(58) Field of Classification Search
CPC ....... A61B 17/545; A61B 50/20; A61B 50/22; A61B 18/12; A61B 2017/320004;
(Continued)

(56) References Cited

U.S. PATENT DOCUMENTS 1,651,585 A 12/1927 Clair
2,608,032 A 8/1952 Garver
(Continued)

FOREIGN PATENT DOCUMENTS

AT 400 305 12/1995
AU 1 014 299 5/1999
(Continued)

OTHER PUBLICATIONS

International Search Report; Application No. PCT/US2014/24992 (a related PCT of the subject application), dated Jul. 21, 2014.
(Continued)

*Primary Examiner* — Jocelin C Tanner
(74) *Attorney, Agent, or Firm* — Knobbe, Martens, Olson & Bear, LLP

(57) ABSTRACT

According to some embodiments, a method of treating a skin surface of a subject comprises heating a skin surface, abrading native skin tissue of a subject using a microdermabrasion device, wherein using the microdermabrasion device comprises moving the microdermabrasion device relative to the skin surface while simultaneously delivering at least one treatment fluid to the skin surface being treated and cooling the abraded skin surface.

14 Claims, 15 Drawing Sheets

Related U.S. Application Data

(60) Provisional application No. 61/791,157, filed on Mar. 15, 2013.

(51) Int. Cl.

| | | |
|---|---|---|
| *A61N 5/06* | (2006.01) | |
| *A61N 7/00* | (2006.01) | |
| *A61B 17/00* | (2006.01) | |
| *A61B 17/32* | (2006.01) | |
| *A61B 17/54* | (2006.01) | |
| *A61B 18/12* | (2006.01) | |
| *A61B 50/20* | (2016.01) | |
| *A61B 50/22* | (2016.01) | |
| *A61N 5/067* | (2006.01) | |

(52) U.S. Cl.
CPC ..... *A61B 18/12* (2013.01); *A61B 2017/00761* (2013.01); *A61B 2017/320004* (2013.01); *A61F 2007/0075* (2013.01); *A61N 5/022* (2013.01); *A61N 5/0616* (2013.01); *A61N 2005/067* (2013.01); *A61N 2007/0034* (2013.01)

(58) Field of Classification Search
CPC . A61B 2017/00761; A61B 2017/00747; A61F 7/007; A61F 2007/0075; A61N 5/0616; A61N 5/022; A61N 2005/067
See application file for complete search history.

(56) References Cited

U.S. PATENT DOCUMENTS

| | | |
|---|---|---|
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,574,239 A | 4/1971 | Sollerud |
| 3,715,838 A | 2/1973 | Young et al. |
| 3,865,352 A | 2/1975 | Nelson et al. |
| 3,866,264 A | 2/1975 | Engquist |
| 3,948,265 A | 4/1976 | Al Ani |
| 3,964,212 A | 6/1976 | Karden |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| 4,216,233 A | 8/1980 | Stein |
| 4,225,254 A | 9/1980 | Holberg et al. |
| 4,289,158 A | 9/1981 | Nehring |
| 4,299,219 A | 11/1981 | Norris, Jr. |
| 4,378,804 A | 4/1983 | Cortese |
| 4,560,373 A | 12/1985 | Sugino et al. |
| 4,646,480 A | 3/1987 | Williams |
| 4,646,482 A | 3/1987 | Chitjian |
| 4,655,743 A | 4/1987 | Hyde |
| 4,676,749 A | 6/1987 | Mabille |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,875,287 A | 10/1989 | Creasy et al. |
| 4,886,078 A | 12/1989 | Shiffman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| 4,957,747 A | 9/1990 | Stiefel |
| 5,006,004 A | 4/1991 | Dirksing et al. |
| 5,006,339 A | 4/1991 | Bargery et al. |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,222,956 A | 6/1993 | Waldron |
| 5,242,433 A | 9/1993 | Smith et al. |
| 5,254,109 A | 10/1993 | Smith et al. |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Clarke |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore et al. |
| 5,813,416 A | 9/1998 | Rudolph |
| 5,817,050 A | 10/1998 | Klein |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |

(56) References Cited

U.S. PATENT DOCUMENTS

| | | |
|---|---|---|
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Park et al. |
| 6,183,451 B1 | 2/2001 | Mehl, Sr. et al. |
| 6,183,483 B1 | 2/2001 | Chang |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 | 8/2001 | Muldner |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabei et al. |
| 6,332,886 B1 | 12/2001 | Green et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,511,486 B2 | 1/2003 | Mercier et al. |
| 6,514,262 B1 | 2/2003 | Di Fiore et al. |
| 6,527,783 B1 | 3/2003 | Ignon |
| 6,535,761 B2 | 3/2003 | Bernabei |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| 6,685,853 B1 | 2/2004 | Angelopoulous et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| 6,800,083 B2 | 10/2004 | Hiblar et al. |
| 6,869,611 B1 | 3/2005 | Kligman et al. |
| 6,905,487 B2 | 6/2005 | Zimmerman |
| 6,911,031 B2 | 6/2005 | Muldner |
| 6,924,649 B2 | 8/2005 | Knoedgen |
| 6,926,681 B1 | 8/2005 | Ramey et al. |
| 6,942,649 B2 | 9/2005 | Ignon et al. |
| 6,960,206 B2 | 11/2005 | Keane |
| 7,001,355 B2 | 2/2006 | Nunomura et al. |
| 7,004,933 B2 | 2/2006 | McDaniel |
| 7,044,938 B2 | 5/2006 | La Bianco et al. |
| 7,052,503 B2 | 5/2006 | Bernabei |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| 7,276,051 B1 | 10/2007 | Henley et al. |
| 7,293,930 B2 | 11/2007 | Chuang |
| 7,314,326 B2 | 1/2008 | Rosenberg |
| 7,316,657 B2 | 1/2008 | Kleinhenz et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,427,273 B2 | 9/2008 | Mitsui |
| 7,458,944 B2 | 12/2008 | Liste et al. |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| 8,221,437 B2 | 7/2012 | Waldron et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| 8,814,836 B2 | 8/2014 | Ignon et al. |
| 9,056,193 B2 | 6/2015 | Ignon et al. |
| 9,468,464 B2 | 10/2016 | Shadduck |
| 9,474,886 B2 | 10/2016 | Ignon et al. |
| 9,486,615 B2 | 11/2016 | Ignon et al. |
| 9,498,610 B2 | 11/2016 | Ignon et al. |
| 9,550,052 B2 | 1/2017 | Ignon et al. |
| 9,566,088 B2 | 2/2017 | Ignon et al. |
| 9,642,997 B2 | 5/2017 | Ignon et al. |
| 9,662,482 B2 | 5/2017 | Ignon et al. |
| 9,775,646 B2 | 10/2017 | Shadduck |
| 9,814,868 B2 | 11/2017 | Ignon et al. |
| 10,035,007 B2 | 7/2018 | Ignon et al. |
| 2001/0023351 A1 | 9/2001 | Eilers |
| 2001/0049511 A1 | 12/2001 | Coleman et al. |
| 2002/0016601 A1 | 2/2002 | Shadduck |

(56) References Cited

U.S. PATENT DOCUMENTS

| | | | |
|---|---|---|---|
| 2002/0041891 A1 | 4/2002 | Cheski | |
| 2002/0058952 A1 | 5/2002 | Weber et al. | |
| 2002/0107527 A1 | 8/2002 | Burres | |
| 2002/0128663 A1 | 9/2002 | Mercier et al. | |
| 2002/0133110 A1 | 9/2002 | Citow | |
| 2002/0133176 A1 | 9/2002 | Parkin et al. | |
| 2002/0151826 A1 | 10/2002 | Ramey et al. | |
| 2002/0151908 A1 | 10/2002 | Mallett, Sr. et al. | |
| 2002/0188261 A1 | 12/2002 | Hruska | |
| 2003/0012415 A1 | 1/2003 | Cossel | |
| 2003/0018252 A1 | 1/2003 | Duchon et al. | |
| 2003/0060834 A1 | 3/2003 | Muldner | |
| 2003/0093040 A1 | 5/2003 | Mikszta et al. | |
| 2003/0093089 A1 | 5/2003 | Greenberg | |
| 2003/0097139 A1 | 5/2003 | Karasiuk | |
| 2003/0167032 A1 | 9/2003 | Ignon | |
| 2003/0187462 A1 | 10/2003 | Chang | |
| 2003/0208159 A1* | 11/2003 | Ignon | A61B 17/545 604/140 |
| 2003/0212127 A1 | 11/2003 | Glassman et al. | |
| 2003/0212415 A1 | 11/2003 | Karasiuk | |
| 2004/0010222 A1 | 1/2004 | Nunomura et al. | |
| 2004/0010269 A1 | 1/2004 | Grimes et al. | |
| 2004/0015139 A1 | 1/2004 | La Bianco | |
| 2004/0087972 A1 | 5/2004 | Mulholland et al. | |
| 2004/0092895 A1 | 5/2004 | Harmon | |
| 2004/0092959 A1 | 5/2004 | Bernaz | |
| 2004/0097967 A1 | 5/2004 | Ignon | |
| 2004/0122447 A1 | 6/2004 | Harmon et al. | |
| 2004/0127914 A1 | 7/2004 | Chung | |
| 2004/0143274 A1 | 7/2004 | Shadduck | |
| 2004/0162565 A1 | 8/2004 | Carson et al. | |
| 2004/0166172 A1 | 8/2004 | Rosati et al. | |
| 2004/0219179 A1 | 11/2004 | McDaniel | |
| 2004/0236291 A1 | 11/2004 | Zelickson et al. | |
| 2004/0243149 A1 | 12/2004 | Lee, Jr. | |
| 2004/0254587 A1 | 12/2004 | Park | |
| 2004/0267285 A1 | 12/2004 | Chang | |
| 2005/0037034 A1 | 2/2005 | Rhoades | |
| 2005/0038448 A1 | 2/2005 | Chung | |
| 2005/0059940 A1 | 3/2005 | Weber et al. | |
| 2005/0084509 A1 | 4/2005 | Bernstein | |
| 2005/0148958 A1 | 7/2005 | Rucinski | |
| 2005/0203111 A1 | 9/2005 | David | |
| 2005/0209611 A1 | 9/2005 | Greenberg | |
| 2005/0283176 A1 | 12/2005 | Law | |
| 2006/0002960 A1 | 1/2006 | Zoeteweij et al. | |
| 2006/0116674 A1 | 6/2006 | Goble et al. | |
| 2006/0161178 A1 | 7/2006 | Lee | |
| 2006/0189964 A1 | 8/2006 | Anderson | |
| 2006/0191562 A1 | 8/2006 | Numomura | |
| 2006/0200099 A1 | 9/2006 | La Bianco et al. | |
| 2006/0200172 A1 | 9/2006 | Shadduck | |
| 2006/0200173 A1 | 9/2006 | Shadduck | |
| 2006/0212029 A1 | 9/2006 | Arcusa Villacampa et al. | |
| 2006/0253125 A1 | 11/2006 | Ignon | |
| 2006/0264893 A1 | 11/2006 | Sage, Jr. et al. | |
| 2007/0005078 A1 | 1/2007 | Hart et al. | |
| 2007/0043382 A1 | 2/2007 | Cheney | |
| 2007/0065515 A1 | 3/2007 | Key | |
| 2007/0088371 A1 | 4/2007 | Karasiuk | |
| 2007/0123808 A1 | 5/2007 | Rhoades | |
| 2007/0154502 A1 | 7/2007 | Hattendorf et al. | |
| 2007/0156124 A1 | 7/2007 | Ignon et al. | |
| 2007/0178121 A1 | 8/2007 | First et al. | |
| 2007/0198031 A1 | 8/2007 | Kellogg | |
| 2007/0208353 A1 | 9/2007 | Shadduck | |
| 2007/0239173 A1 | 10/2007 | Khalaj | |
| 2008/0027328 A1 | 1/2008 | Klopotek et al. | |
| 2008/0091179 A1 | 4/2008 | Durkin et al. | |
| 2008/0103563 A1 | 5/2008 | Powell | |
| 2008/0119781 A1 | 5/2008 | King | |
| 2008/0132914 A1 | 6/2008 | Bossard et al. | |
| 2008/0139974 A1 | 6/2008 | Da Silva | |
| 2008/0154161 A1 | 6/2008 | Abbott | |
| 2008/0193493 A1 | 8/2008 | Rhoades | |
| 2008/0200861 A1 | 8/2008 | Shalev et al. | |
| 2008/0208146 A1 | 8/2008 | Brandwein et al. | |
| 2008/0214987 A1 | 9/2008 | Xu | |
| 2008/0215068 A1 | 9/2008 | Hart et al. | |
| 2008/0221548 A1 | 9/2008 | Danenberg et al. | |
| 2008/0243039 A1 | 10/2008 | Rhoades | |
| 2008/0287864 A1 | 11/2008 | Rosenberg | |
| 2008/0300529 A1 | 12/2008 | Reinstein | |
| 2008/0300552 A1 | 12/2008 | Cichocki et al. | |
| 2009/0048557 A1 | 2/2009 | Yeshurun et al. | |
| 2009/0053390 A1 | 2/2009 | Sakou et al. | |
| 2009/0062815 A1 | 3/2009 | Karasiuk et al. | |
| 2009/0099091 A1 | 4/2009 | Hantash | |
| 2009/0099093 A1 | 4/2009 | Hantash | |
| 2009/0124985 A1 | 5/2009 | Hasenoehrl et al. | |
| 2009/0138026 A1 | 5/2009 | Wu | |
| 2009/0177171 A1* | 7/2009 | Ignon | A61B 17/54 604/289 |
| 2009/0192442 A1 | 7/2009 | Ignon et al. | |
| 2009/0222023 A1 | 9/2009 | Boone, III et al. | |
| 2010/0045427 A1 | 2/2010 | Boone, III et al. | |
| 2010/0049177 A1 | 2/2010 | Boone, III et al. | |
| 2010/0049210 A1 | 2/2010 | Boone, III et al. | |
| 2010/0217357 A1 | 8/2010 | Da Silva | |
| 2010/0305495 A1 | 12/2010 | Anderson et al. | |
| 2011/0054490 A1 | 3/2011 | Hart | |
| 2011/0066162 A1 | 3/2011 | Cohen | |
| 2011/0082415 A1 | 4/2011 | Ignon et al. | |
| 2012/0041338 A1 | 2/2012 | Chickering, III et al. | |
| 2012/0136374 A1 | 5/2012 | Karasiuk | |
| 2013/0004230 A1 | 1/2013 | Kirk, III et al. | |
| 2013/0018317 A1 | 1/2013 | Bobroff et al. | |
| 2013/0066336 A1 | 3/2013 | Boone, III et al. | |
| 2013/0096577 A1 | 4/2013 | Shadduck | |
| 2013/0144280 A1 | 6/2013 | Eckhouse et al. | |
| 2013/0158547 A1 | 6/2013 | David | |
| 2014/0343481 A1 | 11/2014 | Ignon | |
| 2014/0343574 A1 | 11/2014 | Ignon et al. | |
| 2015/0032047 A1 | 1/2015 | Ignon et al. | |
| 2015/0230825 A1 | 8/2015 | Shadduck | |
| 2015/0231379 A1 | 8/2015 | Ignon et al. | |
| 2015/0265822 A1 | 9/2015 | Ignon et al. | |
| 2015/0290442 A1 | 10/2015 | Ignon et al. | |
| 2016/0038183 A1 | 2/2016 | Ignon et al. | |
| 2017/0036002 A1 | 2/2017 | Ignon et al. | |
| 2017/0065801 A1 | 3/2017 | Ignon et al. | |
| 2017/0209894 A1 | 7/2017 | Sporrer | |
| 2017/0224972 A1 | 8/2017 | Ignon et al. | |
| 2017/0245876 A1 | 8/2017 | Ignon et al. | |
| 2017/0266424 A1 | 9/2017 | Ignon et al. | |
| 2017/0319835 A1 | 11/2017 | Ignon et al. | |
| 2017/0319836 A1 | 11/2017 | Ignon et al. | |
| 2017/0333689 A1 | 11/2017 | Ignon et al. | |

FOREIGN PATENT DOCUMENTS

| | | |
|---|---|---|
| CA | 2 340 154 | 9/2002 |
| DE | 59 95 21 | 7/1934 |
| DE | 24 15 633 | 10/1975 |
| DE | 33 38 057 | 8/1984 |
| DE | 34 21 390 A1 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 A1 | 11/2005 |
| EP | 0 258 901 | 9/1987 |
| EP | 0 564 392 | 3/1993 |
| EP | 0 784 997 | 7/1997 |
| EP | 2106780 | 3/2016 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |

(56) References Cited

FOREIGN PATENT DOCUMENTS

| | | |
|---|---|---|
| IT | 118 49 22 | 3/1985 |
| JP | H05-042060 | 2/1993 |
| JP | 1993-088552 | 12/1993 |
| JP | 09-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |
| JP | 2006-204767 | 10/2006 |
| KR | 20-0280320 | 7/2002 |
| KR | 10-20070070173 | 7/2007 |
| WO | WO 1994/024980 | 11/1994 |
| WO | WO 1997/11650 | 4/1997 |
| WO | WO 2000/015300 | 3/2000 |
| WO | WO 2001/93931 | 12/2001 |
| WO | WO 2003/073917 | 9/2003 |
| WO | WO 2004/037098 | 5/2004 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2009/088884 | 7/2009 |
| WO | WO 2009/097451 | 8/2009 |
| WO | WO 2012/145667 | 10/2012 |

OTHER PUBLICATIONS

Cox III et al., *Decreased Splatter in Dermabrasion*, Arch Facial Plastic Surgery, Jan.-Mar. 2000, vol. 2, pp. 23-26.

Ditre et al., *Effect of α-hydroxy acids on photoaged skin: A pilot clinical, histologic, and ultrastructural study*, Journal of American Academy of Dermatology, Feb. 1996, vol. 34, No. 2, Part 1, pp. 187-195.

Harris et al., *Combining Manual Dermasanding with Low Strength Trichloroacetic Acid to Improve Antinically Injured Skin*, The Journal of Dermatologic Surgery and Oncology, Jul. 1994, vol. 20, No. 7, pp. 436-442.

Microdermabrader Pepita Instruction Manual, Mattioli Engineering S.R.L., PEP_USA2.doc Rev 1.1, Sep. 29, 1997.

* cited by examiner

DEVICES, SYSTEMS AND METHODS FOR TREATING THE SKIN

CROSS-REFERENCE TO RELATED APPLICATIONS & INCORPORATION BY REFERENCE

This application is a continuation of U.S. patent application Ser. No. 14/211,290, filed Mar. 14, 2014, which claims the priority benefit under 35 U.S.C. § 119(e) of U.S. Provisional Application No. 61/791,157, filed Mar. 15, 2013, the entireties of both of which are hereby incorporated by reference herein. The entireties of U.S. patent application Ser. No. 12/346,582, filed Dec. 30, 2008 and issued on Jan. 1, 2013 as U.S. Pat. No. 8,343,116, and U.S. patent application Ser. No. 11/392,348, filed Mar. 29, 2006 and issued on Nov. 1, 2011 as U.S. Pat. No. 8,048,089, are hereby incorporated by reference herein and made a part of the present specification.

BACKGROUND

Field

This application relates generally to skin treatment, and more specifically, to apparatuses, systems and methods for treating a person's skin.

Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

SUMMARY

According to some embodiments, a method of treating a skin surface of a subject comprises heating a skin surface, abrading native skin tissue of a subject using a microdermabrasion device, wherein using the microdermabrasion device comprises moving the microdermabrasion device relative to the skin surface while simultaneously delivering at least one treatment fluid to the skin surface being treated and cooling the abraded skin surface.

According to some embodiments, heating and cooling the skin surface is performed using a thermal conditioning handheld assembly. In one embodiment, the thermal conditioning handheld assembly is configured to be selectively heated or cooled conductively (e.g., using at least one thermoelectric device) within a thermal recharging station. In some embodiments, the at least one treatment fluid is delivered to the skin surface using and through the microdermabrasion device. The method further comprising exposing the skin surface to at least one additional treatment (e.g., exposure to a source of energy, such as, radiofrequency, ultrasound, microwave, laser, etc.).

According to some embodiments, a skin surface of a subject comprising abrading native skin tissue of a subject using a microdermabrasion device, wherein using the microdermabrasion device comprises moving the microdermabrasion device relative to the skin surface while simultaneously delivering at least one treatment fluid to the skin surface being treated and exposing the skin surface to at least one additional treatment procedure.

According to some embodiments, the at least one additional treatment procedure comprises exposing the skin surface to an energy source. In one embodiment, the energy source comprises at least one of radiofrequency, ultrasound, microwave, laser and/or the like. In some embodiments, the at least one additional treatment procedure comprises delivering air to the skin surface. In some embodiments, air is delivered to the skin surface by and through the microdermabrasion device. In one embodiment, the at least one additional treatment procedure comprises exposing the skin surface to light. In some embodiments, the at least one additional treatment procedure comprises heating or cooling the skin surface.

According to some embodiments, a microdermabrasion device for treating skin comprises a handpiece assembly having a distal end and a proximal end. The handpiece assembly includes at least one delivery conduit and at least one waste conduit. The microdermabrasion device additionally comprises a tip configured to be positioned along the distal end of the handpiece assembly, wherein the tip is adapted to contact skin surface. According to some embodiments, the microdermabrasion device further includes a flow control device or feature included within the handpiece assembly to regulate the flow of fluids through the delivery conduit. In several embodiments, the tip comprises a lip, a first opening in fluid communication with the fluid delivery conduit and a second opening in fluid communication with the waste conduit. In one embodiment, the device includes one or more abrasive elements positioned along a distal end of the tip, wherein the abrasive elements are configured to selectively remove skin as the tip is moved relative to a skin surface. In some embodiments, the first opening, the second opening and the abrasive elements of the tip are positioned within an interior of an outer periphery formed by the lip. In some embodiments, the waste conduit is in fluid communication with a vacuum source to selectively remove debris away from the tip. In one embodiment, the delivery conduit is in fluid communication with the at least one waste conduit and the vacuum source when the lip contacts a skin surface. In some embodiments, the delivery conduit is configured to selectively deliver at least one time-release material to the skin surface being treated.

According to some embodiments, the flow control device comprises a valve (e.g., a needle valve). In some embodiments, the abrasive element comprises a protruding member, a spiral ridge or an abrasive surface. In other embodiments, the abrasive element comprises an abrasive disc, an abrasive surface and/or any other member that is configured to be separated from the tip or that is configured to be permanently attached to the tip. In one embodiment, the tip is removable from the handpiece assembly. In other embodiments, the time-release material comprises a plurality of microcapsules, capsules or other enclosures configured to release their internal contents at various times following delivery to the skin surface. In some embodiments, the time-release material comprises salicylic acid. In other embodiments, the time-release material comprises one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.), either alone or in combination with one another.

In one embodiment, the time-release material is impregnated along at least a portion of the tip. In other embodiments, the time-release material is initially contained within a cartridge or other container that is in fluid communication with the delivery conduit when the cartridge or other container is secured to the handpiece assembly. In other embodiments, the time release material is delivered to the tip of the handpiece without any prior dilution or premixing. In some embodiments, the handpiece assembly comprises a recess configured to removably receive a cartridge, wherein an internal content of the cartridge is placed in fluid communication with the delivery conduit when the cartridge is secured within the recess of the handpiece assembly. In some embodiments, the cartridge or container comprises a movable piston therein, wherein the movable piston configured to urge an internal content of the cartridge toward an outlet of the cartridge. In some embodiments, the cartridge or container comprises an airless pump design or configuration. In one embodiment, the time-release material is configured to treat a skin disorder or condition (e.g., acne, oily or dry skin, etc.).

According to certain arrangements, a device for treating a skin surface includes a handpiece assembly having a distal end and a proximal end such that the handpiece assembly comprises at least one delivery conduit and at least one waste conduit. The device additionally comprises a tip configured to be positioned along the distal end of the handpiece assembly, such that the tip is adapted to contact the skin surface being treated. According to certain embodiments, the tip comprises a peripheral lip, a first opening in fluid communication with the fluid delivery conduit and a second opening in fluid communication with the waste conduit and an abrasive element or surface positioned along a distal end of the tip, said abrasive element or surface configured to remove skin. In one embodiment, the first opening, the second opening and the abrasive element of the disc are positioned along an interior of the peripheral lip. In another arrangement, one or more waste conduits are configured to be in fluid communication with a vacuum to selectively remove debris away from the tip. In other configurations, a delivery conduit is placed in fluid communication with the waste conduit and the vacuum when the peripheral lip contacts a skin surface. In yet other embodiments, one or more time-release materials are configured to be delivered to the skin surface being treated.

In some embodiments, the handpiece assembly comprises a housing having a clamshell design. In one embodiment, a housing of the handpiece assembly comprises two or more portions that are configured to removably or permanently attach to each other (e.g., using screws, other fasteners, snap fit or friction fit connections, adhesives, welds and/or any other connection method or device). In some embodiments, the two or more portions of the housing are configured to be manufactured using an injection molding procedure or any other molding or manufacturing process (e.g., compression molding, thermoforming, extrusion, etc.). In one embodiment, the two portions or more portions of the housing comprise a plastic, metal, alloy and/or any other synthetic or natural material.

According to other embodiments, the device additionally includes a valve configured to control a flowrate of a fluid being delivered through the fluid delivery conduit to the tip.

In another arrangement, the abrasive element or structure comprises one or more protruding members, spiral ridges and/or abrasive surfaces. In certain embodiments, the time-release material comprises a plurality of microcapsules or capsules configured to release their internal contents at various times following delivery to the skin surface. In one embodiment, the time-release materials comprise one or more of the following: peptides, amino acids, UVA and/or UVB sunblocks, other sunblocking agents, skin tightening agents, hyaluronic acid (HA), other hydration agents, hair removal or hair growth suppression agents, medicaments and pharmaceuticals, combinations thereof and/or any other substance. In other arrangements, time-release materials are impregnated along at least a portion of the tip. In yet other embodiments, the cartridge or other container is in fluid communication with the handpiece assembly. In certain embodiments, the time-release materials are configured to be released to the skin surface after contact with water or another dilutant. In other arrangements, the time-release materials are configured to treat acne or another skin disorder.

According to certain embodiments of the present application, a handpiece assembly for treating a skin surface comprises a recess configured to receive a cartridge or other container. The cartridge or other container comprises one or more treatment materials, such as, for example, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In one embodiment, the handpiece assembly comprises a valve or other flow control device or feature to enable a user to selectively regulate a flowrate of a treatment material through the handpiece assembly. In other embodiments, the cartridge or other container comprises an inlet configured to be in fluid communication with water, saline, another dilutant or dissolvent or another fluid. The water, saline, another dilutant or dissolvent or another fluid is configured to be delivered through the inlet and to an interior of the cartridge so as to mix or combine with a treatment material contained therein. In some embodiments, the treatment material contained within the cartridge or container is a liquid, solid, gel, granulated material or concentrated solution. In some embodiments, one or more treatment fluids are conveyed from an outlet of the cartridge or container to a tip attached to a distal end of the handpiece assembly.

According to certain arrangements, treatment materials that are provided to the skin interface during a dermabrasion procedure are configured to be released or otherwise made available to a user's skin over a pre-selected, relatively extended time period. Such time release materials can be provided in the form of microcapsules, other capsules or enclosures and/or the like.

Regardless of the form in which they are provided (e.g., within microcapsules or other enclosures), time-release products or materials can be delivered to a skin surface directly through a cartridge or other container. Such a cartridge can be positioned within a handpiece assembly, such as, for example, those illustrated in FIGS. 1-4F, 13A-16B and 18B herein. Cartridges or other containers containing such time-release materials can be provided in various locations of a handpiece assembly, including, without limitation, a recess of the main portion, underneath or near a removable tip and/or the like. In certain embodiments, a cartridge or other container containing one or more time-release materials is separate from the handpiece assembly. For example, as illustrated in FIG. 18A, such a cartridge or other container can be placed along a delivery line, which selectively supplies fluids and/or other materials through the cartridge to a handpiece assembly. In other arrangements, such as, for example, those illustrated in FIGS. 6B, 7, 17 and 20A-23B herein, time-release materials can be provided to the handpiece assembly from one or more upstream containers or other sources via a delivery line. By way of example, in accordance with the configuration depicted herein in FIGS. 7 and 17, time-release and/or other products and substances can be placed within one or more containers of a manifold system. Such materials can be subsequently delivered through a handpiece assembly using one or more conduits to the skin area being treated.

In yet other arrangements, time-release materials are advantageously provided, either alone or in combination with one or more other substances, within a recess, cavity or other opening or a tip or other portion of a skin treatment system. For example, such recesses can be provided along a distal surface of the tip, as illustrated in FIGS. 12A-12C and discussed in greater detail herein. In certain embodiments, one or more time-release materials are embedded, impregnated, placed, stored and/or otherwise disposed on one or more surfaces or areas of the tip or other portion or component of the skin treatment system (e.g., the foam pads of FIG. 19A-20B). Such time-release materials, which may be provided alone or in combination with any other materials, can comprise microcapsules, other capsules, solids, semi-solids, other dried substances, gels, concentrated solutions and/or the like. In some arrangements, time-release materials and/or other substances are provided in capsules (e.g., microcapsules), caps, loose form (e.g., positioned on or within a recess, other portion of the tip, within a cartridge or other container, adhered to one or more surfaces, etc.), as a tablet, pill, disc or other dissolvable solid, saturated within a foam pad or other sponge-like material and/or the like.

Regardless of where the time-release materials are positioned relative to the handpiece assembly (e.g., within a cartridge or other container, within or outside of a handpiece assembly, in a recess or other opening of a tip or other portion of a handpiece assembly, within a foam pad, on a surface of a tip or other portion of a handpiece assembly, etc.), water (e.g., distilled, tap water, filtered, etc.), saline, other dilutants and/or other fluids can be used to selectively dissolve, liquefy, melt, soften, dilute or otherwise prepare the time-release and/or any other materials. Accordingly, the desired salicylic acid, other anti-acne materials, human growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, amino acids, other acids, anesthetics, UVA and/or UVB sunblocks, other sunblocking agents, skin tightening agents, hyaluronic acid (HA), other hydration agents, hair removal or hair growth suppression agents, medicaments and pharmaceuticals, other non-active or active compounds, other fluids or materials, combination or mixtures thereof and/or any other substance can be advantageously provided to the skin surface being treated, as desired or required.

According to certain embodiments, time-release materials include one or more active ingredients that target specific skin conditions or types. For instance, a time-release product used to help control skin acne can include salicylic acid. The salicylic acid can be provided alone or in combination with one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.).

Time-release salicylic acid capsules (e.g., microcapsules) and/or any other active or non-active ingredients included in a skin treatment material can be encapsulated within a solid binder, such as, for example, soap or gel. Thus, when water or another fluid is added to the material, the treatment material can at least partially dissolve, advantageously releasing capsules onto the skin surface. The capsules can be configured to release their internal contents at different time intervals after being deposited on or near a person's skin.

Alternatively, as discussed in greater detail herein, such microcapsules or other time-release materials can be provided within a cartridge, another container, a recess or other opening and/or the like. According to certain embodiments, the microcapsules or other time-release materials are included within a binder or are provided in loose form (e.g., as a solid, within a liquid, gel, other fluid or other medium, etc.). Thus, time-release materials can be selectively delivered to the skin (or be initially present at a tip-skin interface) in one or more different forms. Regardless of the exact manner in which they are provided to a person's skin, such time-release materials can help target certain skin ailments or conditions (e.g., acne, eczema, psoriasis, etc.), conditions (e.g., dry skin, oily skin, etc.) and/or the like.

In some embodiments, microcapsules and/or other time-release products delivered to the skin surface are configured to be released or otherwise become available to the skin at different times from each other. For example, microcapsules can be adapted to release salicylic acid and/or any other active or non-active ingredients contained therein in various time intervals (e.g., quarter-hour, half-hour, one-hour, two-hour, three-hour, etc.). Accordingly, the desired materials can be provided to a target skin surface to have an effect on such a surface over a longer period of time. This can facilitate a particular treatment procedure by effectively prolonging the overall treatment time-period. For example, in some embodiments, an acne treatment is more effective if salicylic acid is released over a targeted skin surface during a longer time period (e.g., less than 30 minutes, 1 hour, 2 hours, 4 hours, 6 hours, 8 hours, 10 hours, 12 hours, 24 hours, 36 hours, 48 hours, more than 48 hours, etc.).

In one embodiment, time-release materials are provided to a dermabrasion system which is adapted to treat skin having acne or another skin condition. A handpiece assembly having an abrasive distal end, such as, for example, a tip in accordance with any of the arrangements illustrated or otherwise disclosed herein, or equivalents thereof, can be used to treat a skin surface of a patient. As the tip is moved across the target skin area, exfoliated skin, infected waste and/or other materials can be advantageously removed. In addition, the treatment system can be configured to selectively deposit time-release product onto the treated skin before, after and/or contemporaneously with the exfoliation process. As discussed in greater detail herein, the time-release product can be delivered from a cartridge or other container located either within a handpiece assembly or separate from it. In some arrangements, water, saline and/or other dilutants are required to at least partially dissolve or otherwise release such substances (e.g., from a binder, gel, solid, etc.). Salicylic acid and/or any other materials contained within the time-release product (e.g., microcapsules, other capsules, caps, etc.) and/or other materials delivered to the patient's skin can be advantageously released over a longer time-period so as to help prevent or reduce the likelihood of bacterial infection, pain or discomfort, sensitivity to sunlight or other light sources and/or the like.

According to certain arrangements, time-release capsules or other materials containing salicylic acid and/or other skin solutions can be embedded on or near a surface of a tip using a binder. For example, glycerin soap or other base materials or hardening agents can be used to bind the time-release materials. As water, saline or other dilutants or fluids are selectively delivered to the bound materials, time-release materials can dissolve, allowing salicylic acid capsules to be released to a target area of the skin. In one configuration, the time-release materials comprise approximately 30% of the bound mixture by volume, while the soap or other base material and/or hardening agent comprises the remaining approximately 70%. In other embodiments, the volumetric ratio of time-release materials to base materials and hardening agents can be greater or less than 3:7, as required or desired (e.g., less than approximately 1:9, approximately 1:4, 2:3, 1:1, 3:2, 7:3, 4:1, more than approximately 4:1, etc.).

According to certain arrangements, a disc, plate or other member having diamonds or any other abrasive element is removably positioned within an interior region of the tip (e.g., generally between the tip and adjustable distal portion or any other component of the handpiece assembly). Such a disc, which is configured to contact and abrade skin through one or more openings of the tip, can be conveniently removed for cleaning, replacement and/or any other purpose According to other embodiments, a treatment material disposed on or near the tip of the handpiece assembly is configured to be mixed or combined with water, saline or another fluid being delivered through the handpiece assembly to create a treatment fluid. In certain embodiments, the treatment material is provided as a solid, semi-solid, gel, granulated material or concentrated fluid or solution. In some arrangements, the treatment material is positioned within a recess of the tip, between the tip and a main body portion of the handpiece assembly or within the main body portion of the handpiece assembly. In some embodiments, water, saline, treatment fluid or other fluid being conveyed through the handpiece assembly is configured to be heated.

According to certain embodiments of the present application, a device for treating a skin surface comprises a handpiece assembly having a distal end and a proximal end. The handpiece assembly comprises at least one delivery conduit and at least one waste conduit. The handpiece assembly further comprising a recess or other opening configured to receive a cartridge or other container having an interior cavity. In one embodiment, the interior cavity of the cartridge is placed in fluid communication with the fluid delivery conduit when the cartridge is secured within the recess. The device additionally includes a tip positioned along the distal end of the handpiece assembly, such that the tip is configured to contact the skin surface. In certain embodiments, the tip comprises a peripheral lip, a first opening in fluid communication with the fluid delivery conduit and a second opening in fluid communication with the waste conduit and an abrasive element. The first opening, the second opening and the abrasive element are generally positioned along an interior of the peripheral lip. In one embodiment, the waste conduit is configured to be in fluid communication with a vacuum to selectively remove debris away from the tip. In other arrangements, the delivery conduit is placed in fluid communication with the waste conduit and the vacuum when the peripheral lip contacts a skin surface.

In certain arrangements, the device further includes a valve generally positioned between the interior cavity of the cartridge and the fluid delivery conduit. The valve can be adapted to control the flowrate of a fluid being conveyed from the interior cavity of the cartridge to the tip. In other embodiments, the handpiece assembly comprises an adjustable intermediate space positioned generally between the interior cavity of the cartridge and the fluid delivery conduit. In one arrangement, a volume of the adjustable intermediate space can be selectively modified by moving an actuator on the handpiece assembly. In other configurations, the handpiece assembly comprises a stem in fluid communication with the fluid delivery conduit. The stem can be adapted to extend into the interior cavity of a cartridge when the cartridge is positioned with the recess of the handpiece assembly. In other embodiments, the tip is selectively removable from the handpiece assembly. In one arrangement, the abrasive element comprises a plurality of posts, other protruding members, a spiral-shaped ridge, an abrasive surface, a foam pad, another type of pad and/or the like. In some arrangements, the device further includes a heating element configured to selectively heat a fluid being conveyed through the delivery conduit, another interior passage or conduit of the handpiece assembly, the tip, an inlet line and/or the like. In other embodiments, the cartridge comprises an inlet configured to be placed in fluid communication with a delivery source.

According to other arrangements, a skin treatment system includes a handpiece assembly having a distal end and a proximal end. The handpiece assembly comprises a fluid delivery conduit. In one embodiment, the handpiece assembly comprises a first portion and a second portion, with the first portion being selectively movable relative to the second portion. The skin treatment system further includes a tip adapted to contact skin and positioned on the distal end of the handpiece assembly. In one embodiment, the tip comprises a first opening, which is in fluid communication with the fluid delivery conduit, and an abrasive element. The system further comprises an intermediate space generally defined between the first and second portions of the handpiece assembly. Movement of the first portion with respect to the second portion can modify the volume of the intermediate space and generally control the flowrate of a fluid being conveyed through the fluid delivery conduit. In some embodiments, the system further includes an actuator on the handpiece assembly for moving the first portion relative to the second portion.

According to other embodiments, movement of the first portion with respect to the second portion is produced by rotating the second portion relative to the first portion. In some arrangements, the tip is selectively removable from the second portion. In another adaptation, the tip comprises a plurality of posts or protruding members configured to treat skin. In other arrangements, the tip comprises one or more ridges (e.g., spiral-shaped ridges), abrasive surfaces or elements and/or other features or components configured to treat skin. In certain embodiments, the handpiece assembly further comprises a waste channel in fluid communication with a second opening in the tip. In another embodiment, the handpiece assembly includes a recessed area configured to receive a cartridge comprising at least one treatment fluid or material. In other arrangements, the cartridge includes an interior portion which is at least partially defined by a membrane. The membrane can be configured to be pierced by a hollow spike of the first portion of the handpiece assembly when the cartridge is properly inserted within the recessed area, so that the hollow spike is placed in fluid communication with the delivery channel. In certain configurations, the interior portion of the cartridge comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In other arrangements, the device comprises a heater configured to selectively heat a fluid being conveyed through the fluid delivery conduit toward the tip.

According to certain embodiments, a method of providing a treatment fluid to a skin surface while treating said skin surface with a handpiece device includes providing at least one treatment material on or within a handpiece device. In one arrangement, a tip is configured to be removably positioned along a distal end of a main body portion of the handpiece assembly. The tip can be adapted to abrade or otherwise treat skin when moved relative to a skin surface. The treatment method additionally includes directing a first fluid through a delivery passage of the handpiece assembly so that said delivery passage generally contacts at least one treatment material of the tip. In some arrangements, the treatment material is configured to at least partially dissolve, dilute or combine with the first fluid so as to create a desired treatment fluid. Further, the treatment fluid can be configured to be provided to the tip and to the skin surface being treated while a distal end of the tip is being translated over said skin surface.

In some arrangements, the treatment material comprises a solid, granular material, gel or concentrated solution and/or any other material. In other embodiments, the first fluid comprises water (e.g., sterile, tap, distilled, filtered, etc.), saline, other dilutants or dissolvents and/or any other fluid. In other arrangements, the treatment fluid comprises human growth factors, cytokines, soluble collagen, antioxidants or matrix proteins. In another embodiment, the treatment material is positioned in or near the tip, such as, for example, within a post, other protruding member, other recess, underneath the tip and/or like. In other arrangements, the treatment material comprises a disc, tablet, capsule, granular material, gel and/or the like. In one embodiment, the treatment material is configured to be positioned within a cage or other porous container. In other arrangements, the disc, table, capsule or other treatment material is configured to be secured generally between the main body portion and the tip of the handpiece assembly. In one configuration, the method further includes regulating a flowrate of the first fluid by selectively controlling a valve on the handpiece assembly. In another arrangement, the method additionally includes selectively heating the first fluid using a heating member positioned in thermal communication with the delivery passage of the handpiece assembly. In some embodiments, the treatment material is positioned within a cartridge which is configured to be removably secured to a receiving area of the handpiece assembly.

According to some embodiments disclosed in the present application, a device for treating the skin comprises a handpiece assembly having a distal end and a proximal end, a cartridge comprising an interior cavity and a tip on the distal end of the handpiece assembly. The handpiece assembly includes a fluid delivery conduit and a waste conduit. In addition, the cartridge is coupled to the handpiece assembly, with the interior cavity of the cartridge being in fluid communication with the fluid delivery conduit. Further, the tip is configured to contact the skin. The tip comprises a peripheral lip, a first opening in fluid communication with the fluid delivery conduit, a second opening in fluid communication with the waste conduit and an abrasive element. The first opening, the second opening and the abrasive element of the tip are generally positioned within the peripheral lip.

In some embodiments, the device further comprises a valve positioned between the interior cavity of the cartridge and the fluid delivery conduit. In one embodiment, the handpiece assembly comprises an adjustable intermediate space positioned generally between the interior cavity of the cartridge and the fluid delivery conduit. In another arrangement, a volume of the adjustable intermediate space can be selectively modified by moving an actuator on the handpiece assembly. In other embodiments, the handpiece assembly comprises a recessed area configured to receive the cartridge.

According to other embodiments, the handpiece assembly comprises a stem that is in fluid communication with the fluid delivery conduit as the stem is configured to extend into the interior cavity of a cartridge when the cartridge is coupled to the handpiece assembly. In another embodiment, the tip is selectively removable from the handpiece assembly. In some arrangements, the abrasive element comprises a plurality of protruding members. In other embodiments, the tip comprises an abrasive edge.

According to another embodiment, a system for treating the skin comprises a handpiece assembly having a distal end and a proximal end and a tip on the distal end of the handpiece assembly configured to contact the skin. The handpiece assembly includes a fluid delivery conduit and first and second portions. Further, the tip includes a first opening in fluid communication with the fluid delivery conduit and an abrasive element. An intermediate space generally defined between the first and second portions of the handpiece assembly is in fluid communication with the fluid delivery conduit. In one embodiment, movement of the first portion with respect to the second portion modifies the volume of the intermediate space to control a flowrate through the fluid delivery conduit. The system further comprises an actuator on the handpiece assembly for actuating movement between the first portion and the second portion.

In some embodiments, movement of the first portion with respect to the second portion is produced by rotating the second portion relative to the first portion. In other embodiments, the tip is selectively removable from the second portion. In still other arrangements, the tip comprises a plurality of protruding members configured to treat skin. In another embodiment, the tip comprises an abrasive surface configured to treat skin.

According to some embodiments, the handpiece assembly further comprises a waste channel in fluid communication with a second opening in the tip. In another arrangement, the handpiece assembly includes a recessed area configured to receive a cartridge comprising at least one treatment fluid or material. In other embodiments, the cartridge includes an interior portion at least partially defined by a membrane. The membrane is configured to be pierced by a hollow spike of the first portion of the handpiece assembly. Further, the hollow spike is in fluid communication with the delivery channel. In one embodiment, the interior portion of the cartridge comprises human growth factors, cytokines, soluble collagen, antioxidants and/or matrix proteins.

According to other embodiments, the present application discloses a method for treating the skin of a patient with a skin treatment device having a working end that includes an abrading structure configured to engage and abrade skin. The method includes placing the working end of the skin treatment device against the skin of the patient, translating the working end over the skin to abrade a skin surface, providing a treatment fluid to the skin through an opening in the working end and aspirating skin debris from the skin surface through an aspiration opening in the working end of the skin treatment device. In some embodiments, the treatment fluid comprises human growth factors, cytokines, soluble collagen, antioxidants and/or matrix proteins.

According to some embodiments disclosed in the present application, a device for treating the skin comprises a handpiece assembly having a distal end and a proximal end. The handpiece assembly includes a fluid delivery conduit and a waste conduit. In addition, the handpiece assembly is adapted to receive a cartridge having an interior cavity. Further, the device includes a tip attached to the distal end of the handpiece assembly and comprising a surface configured to treat skin. The waste conduit is configured to be in fluid communication with a vacuum source and the fluid delivery conduit is configured to be in fluid communication with an interior cavity of a cartridge when a cartridge is secured to the handpiece assembly.

In some embodiments, the handpiece assembly comprises a flow control feature configured to selectively regulate a flowrate through the fluid delivery conduit. In another arrangement, the handpiece assembly includes a main body portion and an adjustable portion attached to the main body portion. The flow control feature can comprise an adjustable intermediate space generally located between the main body portion and the adjustable portion. In other embodiments, a volume of the adjustable intermediate space can be selectively modified by moving the main body portion relative to the adjustable portion of the handpiece assembly.

In one embodiment, the handpiece assembly comprises a recessed area configured to secure a cartridge. In another arrangement, the handpiece assembly comprises a stem adapted to access an interior cavity of a cartridge when a cartridge is secured to the handpiece assembly. According to some embodiments, the tip is selectively removable from the handpiece assembly. In other embodiments, the tip comprises a plurality of protruding members configured to treat skin. In still other arrangements, the tip comprises an abrasive surface configured to treat skin.

According to another embodiment, a system for treating the skin includes a handpiece assembly. The handpiece assembly comprises a tip configured to treat skin, a first portion and a second portion. The first portion includes a delivery conduit, which has a first longitudinal axis, and is configured to be in fluid communication with at least one fluid source. Further, the second portion includes a distal end and a proximal end, with the proximal end being attached to the main body portion and the distal end being attached to the tip. The second portion includes a delivery channel having a second longitudinal axis and being in fluid communication with the tip and the delivery conduit. In addition, the second portion further comprises a removal channel being in fluid communication with the tip and a suction source. In some embodiments, an intermediate space is generally defined between the first and second portions of the handpiece assembly. Such an intermediate space is in fluid communication with the delivery conduit of the first portion and the delivery channel of the second portion. Further, a volume of the intermediate space is configured to be adjusted by selectively modifying a separation distance between the first portion and the second portion. Accordingly, a flowrate from a fluid source to the tip can be selectively controlled by modifying the separation distance between the first portion and the second portion.

In some embodiments, the separation distance between the first portion and the second portion is modified by rotating the second portion relative to the first portion. In other arrangements, the first longitudinal axis of the delivery conduit is generally offset with the second longitudinal axis of the delivery channel. In one embodiment, the tip is selectively removable from the second portion.

According to some embodiments, the tip comprises a plurality of protruding members configured to treat skin. In other embodiments, the tip comprises an abrasive surface configured to treat skin. In one embodiment, the first portion further comprises a waste channel in fluid communication with the removal channel of the second portion. In another arrangement, the first portion includes a recessed area configured to receive a cartridge comprising at least one treatment fluid or material. In some embodiments, the cartridge includes an interior portion at least partially defined by a membrane which is configured to be pierced by a hollow spike of the first portion of the handpiece assembly. The hollow spike is in fluid communication with the delivery channel. According to other embodiments, the cartridge the interior portion of the cartridge comprises human growth factors, cytokines, soluble collagen, antioxidants or matrix proteins.

According to other embodiments disclosed in the present application, a method of treating the skin comprises providing a handpiece assembly comprising a body and a tip having a distal end. The handpiece assembly includes a delivery conduit and a waste conduit that are in fluid communication with the distal end of the tip. The method further includes placing the delivery conduit of the handpiece assembly in fluid communication with a fluid source for providing at least one treatment fluid to the distal end of the tip and placing the waste conduit of the handpiece assembly in fluid communication with a suction source for removing waste materials from the distal end of the tip. In addition, the method comprises moving the handpiece assembly along a person's skin and activating the suction source to remove a volume of waste materials from the distal end of the tip and to simultaneously deliver a volume of the treatment fluid to the distal end of the tip. In one embodiment, the flowrate at which treatment fluids and/or other materials are delivered to the tip can be varied by a valve or other flow control feature of the handpiece assembly. In some embodiments, the treatment fluid comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance.

BRIEF DESCRIPTION OF THE DRAWINGS

Certain embodiments are disclosed herein having reference to the figures that follow.

DETAILED DESCRIPTION

General

Figure 1:
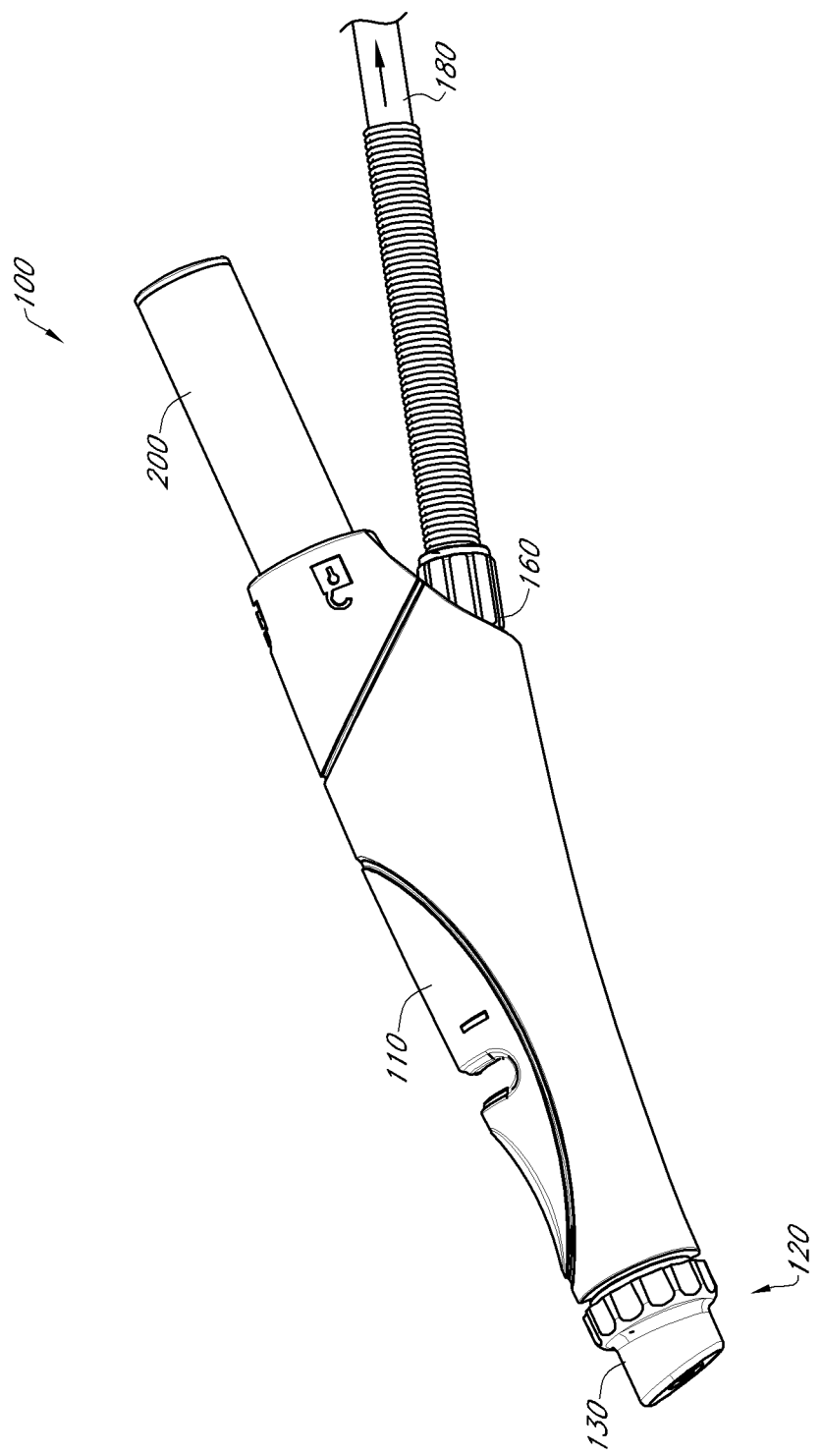
FIG. 1 illustrates a perspective view of a handpiece assembly configured for use with a skin treatment system according to one embodiment.

FIG. 1 illustrates one embodiment of a handpiece assembly 100 configured for use with a skin treatment system. Although the various embodiments of a handpiece assembly have specific relevance to a skin treatment system, the features, advantages and other characteristics disclosed herein may have direct or indirect applicability in other applications, such as, for example, medical devices, mechanical devices and/or the like.

As shown in FIG. 1, a handpiece assembly 100 can include a main body portion 110 configured to receive a tip 130 along its distal end 120. In some embodiments, the tip 130 is removably attached to the distal end of the main body portion 110. Alternatively, however, the tip can be permanently attached to the main body portion 110, as desired or required. The tip can include one or more abrasive features, surfaces and/or the like that are configured to selectively abrade skin when the handpiece assembly 100 is moved relative to a subject's skin. Therefore, the tip can be configured to conduct the microdermabrasion of the targeted skin surface.

Figure 2:
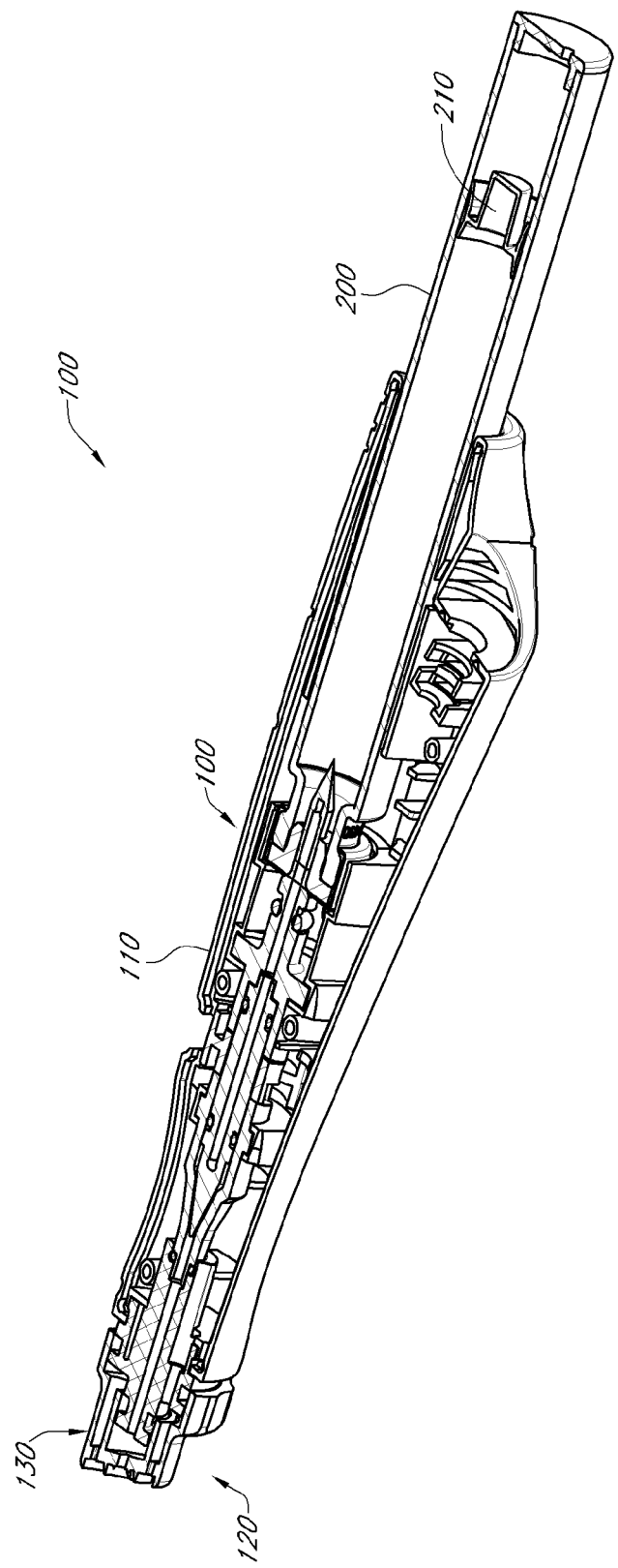
FIG. 2 illustrates a cross-sectional view of the handpiece assembly of FIG. 1.

With continued reference to FIGS. 1 and 2, the handpiece assembly 100 can be sized, shaped and otherwise configured to receive one or more vials or cartridges 200. For example, as shown, the handpiece assembly can include a recess or other opening into which a vial 200 can be placed and secured. Such vials or other containers 200 can include one or more fluids and/or other materials that can be selectively delivered to the subject's skin surface during use.

In some embodiments, the vial or cartridge 200 comprises one or more of the following: human growth factors, cytokines, soluble collagen, antioxidants, matrix proteins, serums, salicylic acid, other anti-acne acids and materials, microcapsules, capsules, other time-release products and substances (e.g., capsules, microcapsules, etc.), water (e.g., distilled, tap water, filtered, etc.), saline, other dilutants or dissolvents, vitamins, chemical exfoliation agents, lotions, soothing agents, brightening or lightening agents (e.g., kojic acid), numbing agents, peptides, acids, anesthetics (e.g., Lidocaine), medicants, other non-active or active compounds, other fluids or materials, combination or mixtures thereof and/or any other substance. Such materials contained in the vial 200 can be selectively delivered to a user's skin while the handpiece assembly 100 is being used. In some embodiments, the handpiece assembly 100 includes an adjustable valve or other flow control feature to enable a user to regulate the rate of delivery of such fluids or other materials to the treatment surface.

In some embodiments, one or more materials can be strategically embedded, impregnated, placed, stored and/or otherwise disposed on one or more surfaces or areas of the tip or other portion or component of the skin treatment system. Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, salicylic acid, other anti-acne acids and materials, microcapsules, capsules, other time-release products and substances, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, water, saline, other dilutants or dissolvents, vitamins, chemical exfoliation agents, lotions, soothing agents, skin brightening or lightening agents, other acids, anesthetics, medicants, other non-active or active compounds, other fluids or materials, combination or mixtures thereof and/or any other substance can be advantageously provided to the skin surface being treated, as desired or required.

In addition, as illustrated in FIG. 1, the handpiece assembly 100 can be connected to a vacuum. For example, the waste conduit 180 of the handpiece assembly can be placed in fluid communication with a suction or vacuum source (not shown) in order to remove exfoliated skin, spent fluids, waste materials and/or other substances away from the treatment surface. As noted above, the handpiece assembly 100 can be configured to receive one or more removable tips 130, which may be selected based upon the specific procedure being performed, the desired result and/or any other considerations. The distal portion 120 of the handpiece assembly 100 can include one or more O-rings 138 or other sealing members to prevent undesirable leaks between the main body portion 110 and the tip 130. Additional details regarding removable tips are provided in U.S. patent application Ser. No. 12/832,663, filed on Jul. 8, 2010 and published as U.S. Publ. No. 2011/0082415 on Apr. 7, 2011, the entirety of which is hereby incorporated by reference herein (see, for example and without limitation, FIGS. 5B and 8A through 16B of the referenced application).

With continued reference to FIGS. 1 and 2, the handpiece assembly 100 can be configured to receive one or more types of vials or cartridges 200. For example, a vial 200 can include, without limitation, a standard or non-standard vial, ampoule or any other container. In some embodiments, serums, salicylic acid, other anti-acne acids and materials, microcapsules, capsules, other time-release products and substances, other fluids and/or other materials contained within the cartridge 200 can be drawn toward the tip 130 using one or more suction sources (e.g., the vacuum source configured to remove waste materials from the tip). In other embodiments, the fluids and/or other materials contained within the cartridge gravity flow toward the tip 130 or are conveyed with the help of a fluid transfer device. The cartridge 200 can be selectively removed from the handpiece assembly 100 when a desired volume or other amount of serum or other material has been delivered to the tip 130.

In other arrangements, two or more different cartridges 200 can be used during a skin treatment procedure. For example, a particular procedure may require the contents (e.g., serums, salicylic acid, other anti-acne acids and materials, microcapsules, capsules, other time-release products and substances, proteins, brightening or lightening agents, peptides, other fluids or substances, etc.) of two or more different cartridges 200. Thus, a user can load and/or unload a combination of cartridges 200 or other containers within a handpiece assembly 100 during a treatment procedure, either at the same time or sequentially (e.g., one after another).

According to some embodiments, as illustrated in FIG. 2, a vial or cartridge 200 can include an internal piston 210 or other movable member. In some embodiments, the piston 210 can urge the internal contents of the vial 200 (e.g., serum, other treatment fluids or materials, etc.) toward the distal end of the vial. The use of such an airless pump design can eliminate or reduce the likelihood that air or other gases will interfere with the consistent delivery of such fluids and/or other materials to the handpiece assembly. Such an airless pump configuration can be used in any of the embodiments disclosed herein.

In such embodiments, the internal volume of the cartridge or vial containing the fluid and/or other material to be selectively delivered to the handpiece assembly can be reduced as fluid and/or other material is expelled from the cartridge. This can help ensure that the internal portion of the cartridge that contains the serum, other liquid and/or other material to be delivered to the handpiece assembly does not include air or other gases. Thus, the treatment media can be consistently and reliably maintained at the distal end of the cartridge interior (e.g., toward the cartridge outlet) during a treatment procedure, regardless if and how a user tilts or otherwise maneuvers the handpiece assembly.

The vial or cartridge 200 can include a main cylindrical portion and a nozzle portion. In some arrangements, the nozzle portion comprises a septum, membrane or other member that can be pierced, punctured or otherwise compromised to access the interior contents of the vial 200 (e.g., serum, other liquids or materials, etc.). The septum can include one or more flexible, rigid and/or semi-rigid materials, such as, for example, rubber, plastic, paper and/or the like.

In some embodiments, a vial or other fluid container 200 can be sized, shaped and otherwise configured to snugly or generally snugly fit within the main body portion 110 of the handpiece assembly 100. Therefore, in some arrangements, the vial or cartridge 200 is secured to the handpiece assembly 100 by friction or by the generally tight tolerances of the recess of the handpiece assembly.

As noted above, the waste conduit 180 (e.g., flexible tubing, hose, etc.) to which the handpiece assembly 100 connects is in fluid communication with a vacuum or other suction source (e.g., pump, other fluid transfer device, etc.). Thus, exfoliated skin, spent fluids and/or other waste materials can be transported away from the tip 130 to a canister (not shown) or other waste source. The rate of transfer of such waste materials can depend on one or more factors, such as, for example, the setting of the vacuum or suction source, the characteristics (e.g., diameter, length, smoothness, etc.) of the various conduits or channels through which the waste materials are conveyed, the viscosity, density and other fluid properties of the waste materials and/or the like.

As discussed herein, in some embodiments, the flow of serums, other fluids and/or any other materials from a vial or cartridge 200 or other source through the handpiece assembly 100 can be regulated by the user using one or more valves or other flow control devices or features.

In some embodiments, a vacuum in fluid communication with the waste conduit 180 can be configured to remove waste materials from the tip 130 and help deliver serums, other fluids and/or any other materials from the vial or cartridge 200 to the tip 130. When the tip 130 is positioned against the subject's skin, suction created by the vacuum source can be transmitted to one or more fluid channel or conduits of the handpiece assembly 100. Such a suction force created within the corresponding channels or conduits of the handpiece assembly remains intact as long as the tip 130 is maintained against or substantially against the subject's skin. Consequently, the suction force crated by the vacuum source can be transferred to one or more fluid delivery channels of the assembly 100, thereby transferring fluids and/or other materials from the vial or other container toward the tip 130.

In some embodiments, serums, other fluids and/or other materials can be delivered to the tip 130 (e.g., from a cartridge, an external source, etc.) through one or more peripheral or other non-centrally located channels, conduits and/or other lines or fittings. For instance, in the handpiece assembly 100 illustrated in FIGS. 1 and 2, such fluids and/or other materials can be routed through one or more internal channels of the assembly and/or waste conduits of the tip. Thus, one or more of the channels, connectors and/or other hydraulic components may need to be reconfigured to adequately place the non-centrally located delivery openings of the tip in fluid communication with corresponding delivery lines of the handpiece assembly 100.

Figure 3:
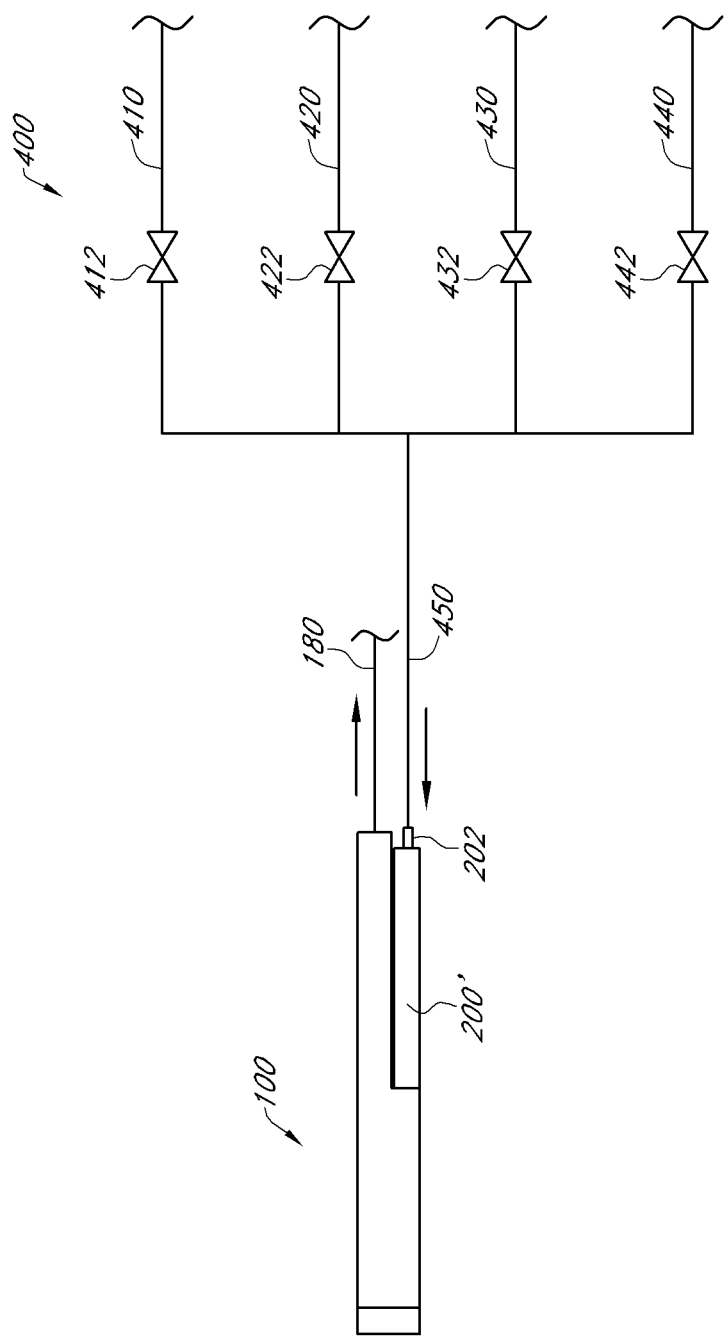
FIG. 3 schematically illustrates a handpiece assembly being in fluid communication with a fluid delivery system or manifold system according to one embodiment.

According to certain embodiments, as illustrated in FIG. 3, a vial, cartridge or other container 200 is placed in fluid communication with a manifold system 400 that may comprise a plurality of individual fluid conduits 410, 420, 430, 440. In turn, one or more of these fluid conduits 410, 420, 430, 440 can be in fluid communication with a separate container (not shown). For example, in some embodiments, such fluid conduits can be in fluid communication with containers of a tower system (see, e.g., FIGS. 9-11). In the illustrated embodiment, the individual fluid lines 410, 420, 430, 440 are in fluid communication with a main fluid conduit 450, which connects to a nozzle 202 along a proximal end of a vial or other container 200 secured within the handpiece assembly 100. One or more of the fluid conduits can comprise a valve 412, 422, 432, 442 or other flow control device or feature to selectively regulate the transfer of fluids and/or other materials to the handpiece assembly 100. In the illustrated arrangement, the manifold system 400 comprises a total of four fluid branches. However, a system can comprise more or fewer fluid branches, as desired or required by a particular application or use.

According to certain embodiments, one or more of the fluid lines fluid conduits of the manifold system illustrated in FIG. 3 are configured to provide a serum, other treatment fluid and/or the like. Alternatively, however, one or more of the conduits can be configured to receive water (e.g., distilled, tap water, filtered, etc.), saline, other dilutants or dissolvents, other fluids and/or the like to the handpiece assembly 100. As discussed in greater detail herein, such fluids can be adapted to contact and dissolve, dilute, liquefy, soften and/or otherwise mix with one or more solids, gels and/or other materials positioned within or on various surfaces or portions of the handpiece assembly 100 (e.g., tip). This can provide a convenient method of providing one or more materials at the skin-tip interface and/or any other location where such materials are desired or required.

As discussed, the vials, cartridges, bottles (e.g., used in towers or other manifold-systems) and/or other fluid sources can include any combination of serums, salicylic acid, other anti-acne acids and materials, microcapsules, capsules, other time-release products and substances, human growth factors, cytokines, collagen, brightening or lightening agents, peptides, peeling agents, acids, antioxidants, matrix proteins, saline, water (e.g., distilled, tap water, filtered, etc.) and/or other liquids or substances, as desired or required by a particular application or use. In certain embodiments, a treatment protocol may require the use of one, two or more different cartridges for a specific procedure. Thus, vials or cartridges 200 can be removed from or inserted into a handpiece assembly prior to or during a particular procedure. Alternatively, when a manifold system is being used to supply fluids to the handpiece assembly, one or more valves can be actuated (e.g., manually or automatically) to enable the desired fluid and/or other substance to be in fluid communication with the handpiece assembly.

In any of the embodiments disclosed herein, a cartridge or vial 200 or a separate bottle contained within a manifold system can advantageously permit a user to deliver human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance to a handpiece assembly from one or more external fluid sources. For example, in some embodiments, the conduit 450 can be placed in fluid communication with one or more containers. Such containers can comprise the desired serums, salicylic acid, other anti-acne acids and materials, microcapsules, capsules, other time-release products and substances, human growth factors, cytokines, collagen, antioxidants, matrix proteins, brightening or lightening agents, peptides, peeling agents, acids, medicants, other fluids or substances, combinations thereof and/or the like, as desired or required by a particular treatment. Thus, the handpiece assembly 100 (e.g., the vial or container 200 of the handpiece assembly) can be used as an interface between the handpiece assembly and a relatively larger source of treatment media. For example, a handpiece assembly 100 can be advantageously placed in fluid communication with a multi-container system such as the one disclosed in U.S. patent application Ser. No. 11/392,348, filed on Mar. 29, 2006 and published on Jul. 5, 2007 as U.S. Publication 2007/0156124, the entirety of which is hereby incorporated by reference herein.

According to certain arrangements, a cartridge 400 includes one or more solids, granular materials, gels, concentrated fluids and/or other substances that are adapted to dissolve, dilute, soften or otherwise mix when contacted by water, saline, other dilutants or dissolvents and/or other fluids. Thus, such materials or other substances can be placed within the cartridge 400 in one or more forms, such as, for example, as powder, granular material, a tablet, a capsule, a pill, other dissolvable solid, a concentrated solution, a gel and/or the like. In other embodiments, such solids, gels and/or other materials can be situated on the tip or other portion of the system (e.g., within a post or recess, adhered to one or more other exposed or hidden surfaces, within a removable cartridge upstream of the handpiece assembly, etc.), impregnated into a foam pad or other member and/or at any other location. Regardless of their exact composition, location and/or other details, such materials and/or other substances can be configured to dissolve, dilute and/or otherwise mix with water, saline and/or other fluids being conveyed through the handpiece assembly 100.

Improved Fluid Penetration and Other Beneficial Effects During Procedures

According to some embodiments, the effectiveness of performing a microdermabrasion procedure can be improved by the delivery of energy, light or air (or other fluid), the delivery of mechanical energy (e.g., acoustic energy, needle penetrations, etc.), the transfer of heat (e.g., to and/or from the skin) and/or the like. This can be conducted concurrently with a microdermabrasion procedure and/or before or after a microdermabrasion as desired or required. In some embodiments, for example, the delivery of energy (e.g., radiofrequency or RF, ultrasound, microwave, etc.), laser, light and/or the like to the skin surface can assist with one or more aspects of the skin treatment process (e.g., its effectiveness, the final result, etc.), healing and recovery. For example, in some embodiments, the application of such ancillary treatments or modalities can improve skin texture and look. In some embodiments, recovery time following a microdermabrasion procedure can be reduced. The application of such treatments or items can also assist with the penetration of the various serums, other liquids and/or other substances used in connection with a skin treatment procedure (e.g., via fluid delivery from a vial or manifold to the tip of the handpiece assembly). The application of energy, mechanical disruption, transfer of heat to or from the skin and/or any other ancillary steps or processes can be used when the microdermabrasion system is being used with or without concurrent (e.g., continuous or intermittent) fluid delivery.

In some embodiments, a handpiece assembly and/or another aspect of a microdermabrasion system is configured to selectively deliver energy, heat (e.g., to or from the skin), air or other fluid, mechanical disruption, light and/or the like to the subject's skin. For example, a handpiece assembly can comprise one or more radiofrequency (RF) electrodes, ultrasound transducers, light, laser or microwave emitters and/or the like. Further, as discussed in greater detail herein with reference to FIGS. 4, 5A and 5B, a handpiece assembly can include one or more lumens or passages that are configured to deliver air or other fluids (e.g., continuously, intermittently at a particular time frequency, etc.) to the skin. In other embodiments, however, the delivery of such energy and/or other items is performed using a separate device or system (e.g., a dedicated energy emitter unit, etc.).

A. Air or Other Fluid Delivery

In some embodiments, it may be beneficial to provide air or other fluid to the skin surface being treated. The air can be delivered at a particular flowrate, pressure, intensity, pulsing rate or frequency and/or time duration to help achieve a particular effect on the skin surface. For example, air or other fluid can be pulsed onto the skin during, before and/or after a microdermabrasion procedure to promote and facilitate the transfer of serums, other liquids and/or other materials at least partially into the subject's skin tissue after exfoliation. In some embodiments, air pulsing can comprise square wave pulsing (e.g., having sequential air delivery and no air delivery phases, one after another, etc.).

Figure 4:
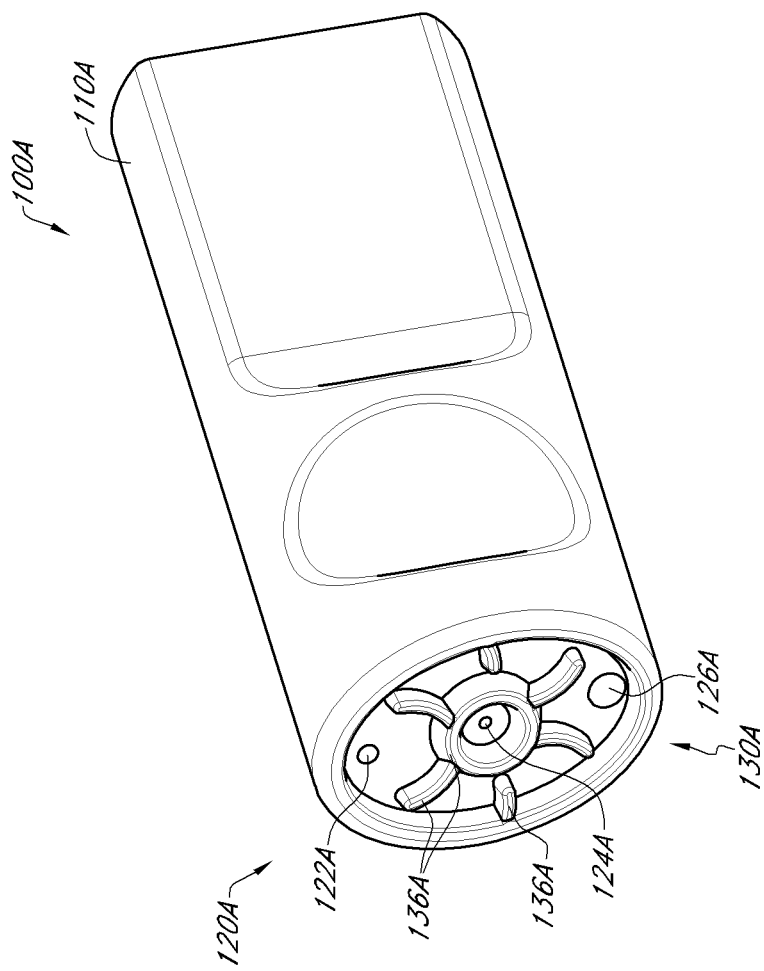
FIG. 4 illustrates a perspective view of one embodiment of a handpiece assembly of a skin treatment device configured to deliver air to the tip.
Figure 5A:
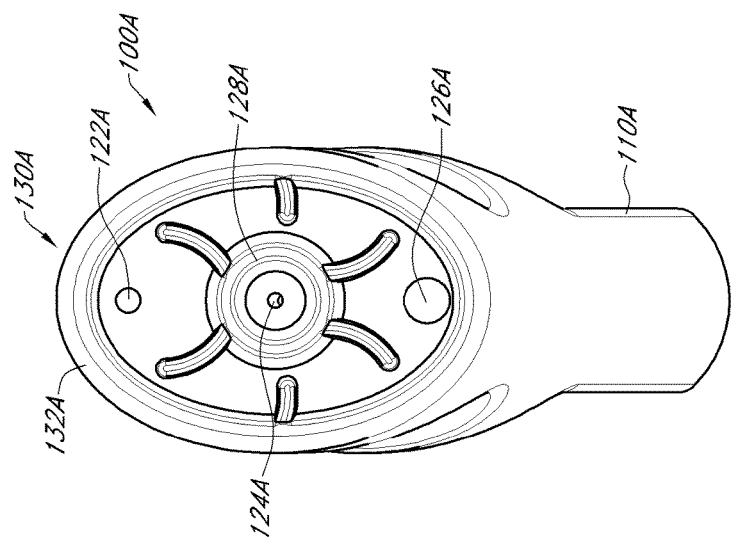
FIGS. 5A-5C illustrate various views of the handpiece assembly of FIG. 4.
Figure 5B:
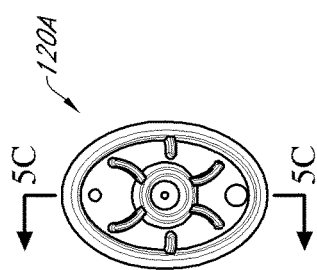

FIG. 4 illustrates one embodiment of a handpiece assembly 100A configured to abrade skin while selectively delivering air (e.g., pulsed air) to the skin surface being treated. As shown, the handpiece assembly 100A can include a main body portion 110A and a distal tip 130A along its distal end 120A. As with other embodiments disclosed herein, the tip 130A can include a peripheral lip or ridge 132A that is configured to engage the subject's skin during use. The tip 130A can comprise one or more skin abrading members, features or portions 136A. Such abrading structures 136A can comprises one or more shapes, designs and the like. For example, in the depicted arrangement, a total of six abrading members 136A are oriented in a generally radial pattern. However, in other embodiments, more or fewer abrading members or structures can be used. Further, such abrading members or structures can vary in type (e.g., posts, abrasive surfaces, ridges, etc.), pattern or layout (e.g., spiral, circular, oval, irregular, etc.), height or other dimensions and/or the like, as desired or required.

With continued reference to FIGS. 4 and 5A-5C, the handpiece assembly 100A can include one or more passages or conduits that extend to or near the tip 130A. For example, as shown, the assembly can include a fluid delivery passage 122A that selectively delivers serums, other liquids and/or other substances to the working surface of the assembly (e.g., from a vial or cartridge secured to the handpiece assembly, from a conduit in fluid communication with a separate tower or manifold system and/or the like. The assembly can also include a vacuum (e.g., negative pressure) or suction passage 126A that is configured to remove spent serums and/or other fluids, together with abraded skin and other debris, when the system is in use and the vacuum source is activated. Additional fluid delivery and/or waste conduit and/or openings can be included in an assembly.

Figure 5C:
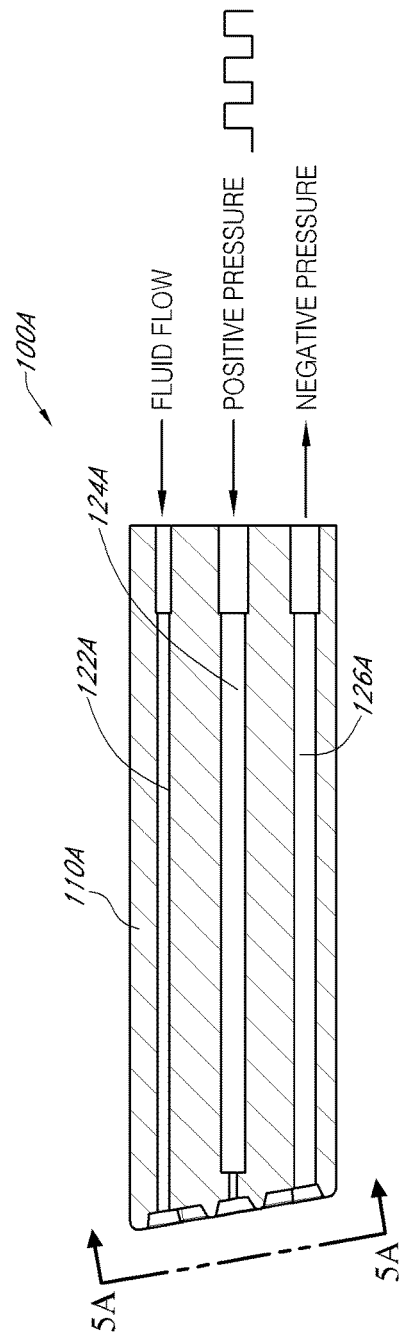

In some embodiments, the handpiece assembly 100A can include one or more air delivery passages 124A that are configured to continuously or intermittently deliver air and/or other fluid to the tip 130A. As illustrated in FIG. 5C, such an air passage 124A can be located along or near the radial center of the assembly and can daylight within an interior lip or ridge 128A along the distal tip. As also shown in the longitudinal sectional view of FIG. 5C, the diameter of the air delivery passage 124A can be decreased or otherwise changed at or near the distal tip 130A. For example, such a narrowing in the diameter can help deliver the air or other fluid at a desired flowrate, velocity and/or pressure.

If, during use, the vacuum source is activated and peripheral lip 132A of the tip 130A is in contact with the subject's skin, the suction passage 126A can create a negative pressure along the distal tip (e.g., along the interior of the peripheral lip), thereby drawing one or more treatment serums or fluids to the tip 130A (e.g., via the fluid delivery passage 122A). Further, in some embodiments, the application of a negative pressure along the tip 130A of the assembly 100A can help draw the subject's skin in contact with the interior lip or ridge 128A. Consequently, only the region along the tip between the peripheral lip 132A and the interior lip 128A may be subjected to the suction created by the vacuum source. Thus, air can be selectively transferred through the air delivery passage 124A of the assembly and onto a subject's skin without losing negative pressure along the annular region of the tip defined by the peripheral and inner lips 132A, 128A. This can advantageously permit the delivery of air to the skin of the subject during a "wet" microdermabrasion process (e.g., one in which treatment fluids are delivered to the working end of the device).

In some embodiments, air is delivered through the air delivery passage 124A in individual puffs. Accordingly, depending on their volume, intensity, pressure and/or other properties, such puffs can help exert an intermittent force along the subject's skin. As noted above, such mechanical or pneumatic agitation of the skin can provide one or more benefits. For example, the resulting force or pressure on the skin can help drive serums, liquids and/or other substances being delivered to the tip (e.g., via the fluid delivery passage) deeper into the skin tissue. The repetitive agitation created by the air puffs can also help loosen dirt, oils and/or other unwanted materials from the pores along the skin surface being treated.

The handpiece assembly 100A can be configured to allow a user to adjust the manner in which air is delivered through the air delivery passage 124 and/or the amount of negative pressure that is applied by the vacuum source through the suction passage 126A (e.g., or the amount negative pressure that is realized along the tip 130A). In some embodiments, the negative pressure within the suction passage 126A is sufficiently high to maintain contact between the subject's skin and the peripheral and inner lips 132A, 128A of the tip 130A during use. This can help maintain a steady and consistent flow of treatment fluids to the working surface while a skin surface is exfoliated or otherwise treated. A sufficiently high vacuum along the tip can also help ensure that the lips 132A, 128A will not lose contact with the skin surface as air is delivered (e.g. in puffs) to the skin surface.

B. Needles and Other Mechanical Penetration and Agitation

According to some embodiments, one or more needles or other piercing members can be used to agitate and/or penetrate certain areas or regions of the subject's skin, before, during or following a microdermabrasion or other skin treatment procedure. The needles or other penetrating members can be moved in and out of adjacent skin tissue over a period of time. Consequently, a plurality of the small diameter passages can be created in the targeted skin tissue, at least temporarily. Such passages can allow serums, other treatment agents and/or other substances that are delivered or otherwise applied to the skin to be advantageously carried deeper into the skin tissue. Additional details regarding the use of needles in connection with skin treatment procedures are found in a provisional application being filed concurrently herewith and titled, "SKIN TREATMENT SYSTEMS AND METHODS USING NEEDLES," the entirety of which is hereby incorporated by reference herein.

In other embodiments, one or more ultrasonic transducers can be positioned relative to the subject's skin before, during and/or after a microdermabrasion procedure so as to selectively deliver acoustic energy to the skin. In some embodiments, the transducers are configured to deliver a relatively low amount of energy to the subject in order to at least partially agitate (e.g., mechanically) the targeted skin tissue. The delivery of ultrasonic energy to the skin may, in certain circumstances, cause the skin tissue to heat.

As with other energy sources disclosed herein, ultrasonic energy can be delivered by a handpiece assembly that comprises one or more transducers. However, in other embodiments, a separate device or component is used to deliver a desired amount of ultrasonic energy to or near the skin tissue.

C. Other Types of Energy Delivery

In other embodiments, the handpiece assembly and/or a separate (e.g., non-integrated) device or system is configured to selectively deliver energy to the targeted skin tissue of the subject. For example, the types of energy-based modalities that can be directed to the skin surface include radiofrequency (RF), microwave, ultrasound and/or the like. As noted above, such energy delivery can be performed before, during and/or after a microdermabrasion or other skin treatment procedure. In some embodiments, the application of such energy to the skin can provide one or more anatomical responses and/or benefits. For example, if the energy applied to the skin is sufficiently high, the skin tissue can be at least partially heated. Such heating and/or other physiological (e.g., biochemical, biological, chemical, etc.) response or effect can, in some embodiments, facilitate the passage of serums and/or other treatment fluids at least partially within the skin tissue.

D. Light Treatment

Figure 6B:
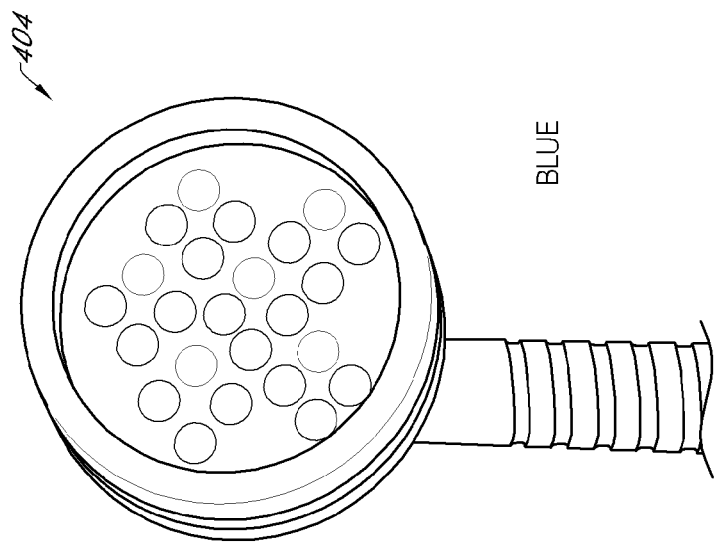
FIGS. 6A and 6B illustrate two different embodiments of a light wand device configured for use with a skin treatment system.
Figure 6A:
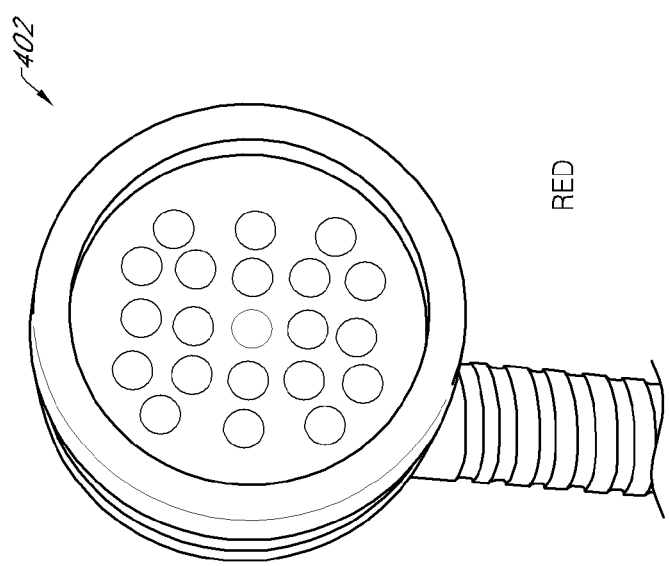

In some embodiments, one or more forms of light can be applied to the skin of the subject, before, during or after a microdermabrasion or other skin treatment procedure. The type of light, its intensity, power, frequency, wavelength, duration of exposure and/or other properties can vary, as desired or required for a particular application or use. In some embodiments, one or more properties of the light source can be varied, during a procedure and/or between procedures. In some embodiments, as illustrated in FIGS. 6A and 6B, the light comprises one or more LEDs or other illumination sources. As with other modalities disclosed herein, the light can be incorporated or attached to a handpiece that is being used for microdermabrasion. However, in other embodiments, the light source is separate and distinct from a microdermabrasion handpiece assembly.

In some embodiments, two or more different types of light sources can be provided as options for the subject or the user performing a procedure on the subject. For example, with reference back to FIGS. 6A and 6B, one of the light wands 402 is configured to emit blue light (e.g., light having a wavelength of approximately 475 nm), while another light wand 404 is configured to emit red light (e.g., light having a wavelength of approximately 650 nm). One or more wands or other light sources can be provided having other target colors. Any other color or light can be emitted, as desired or required. For example, a single light wand can be selected that is adjustable so as to select an exact wavelength of light (in addition to or in lieu of selecting intensity, power and/or any other properties).

One or more light sources can be incorporated directly or indirectly into the handpiece assembly that is configured to perform microdermabrasion. For example, an annular light can be positioned along or near (or embedded partially within) the lip at the distal tip of a microdermabrasion handheld assembly. In other embodiments, the light can be removably mounted along an outside surface of the assembly.

In some embodiments, the use of light is configured to chemically or biochemically "activate" one or more treatment fluids and/or other substances have been or are being delivered to the skin surface of the subject. The activation of certain substances can provide one or more therapeutic or otherwise beneficial results. In other embodiments, the use of red, blue and/or other light can provide one or more direct benefits to the targeted skin tissue. In some embodiments, for example, red light therapy can be used to complement other skin care treatments, while blue light treatment can improve the general appearance of oily and/or acne-prone skin.

In some embodiments, light can be used to heat and/or at least partially modify or affect (e.g., at the cellular level) skin and adjacent tissue of the subject. For example, heat-producing or heat-inducing light source can be directed at the skin for a specific time period, before, during or after a skin treatment procedure (e.g., microdermabrasion). Light sources can include bulbs (e.g., incandescent, fluorescent, low-pressure sodium, high-intensity discharge, etc.), lasers and/or the like. As discussed in greater detail below, heating of the skin can provide one or more benefits to the subject. For example, heating of skin tissue can enable the pores of the subject to open or dilate (e.g., allowing serums and/or other treatment fluids or substances to penetrate deeper into the skin surface). Heating of the skin can also increase blood circulation in the adjacent vessels (e.g., to help improve healing and recovery following a treatment procedure).

E. Thermal Treatment

Exposing the skin to hot and/or cold temperature can assist with various aspects associated with microdermabrasion and other skin treatment techniques and procedures. For example, as discussed herein, heating skin can open the skin's pores, thereby allowing serums, other treatment fluids or materials and/or the like to enhance penetration and migration of such materials into the skin. Further, cooling the skin can cause pores to close, at least partially, allowing therapeutic fluids and/or other materials that previously entered the pores to stay within the skin for a longer time period.

Figure 7A:
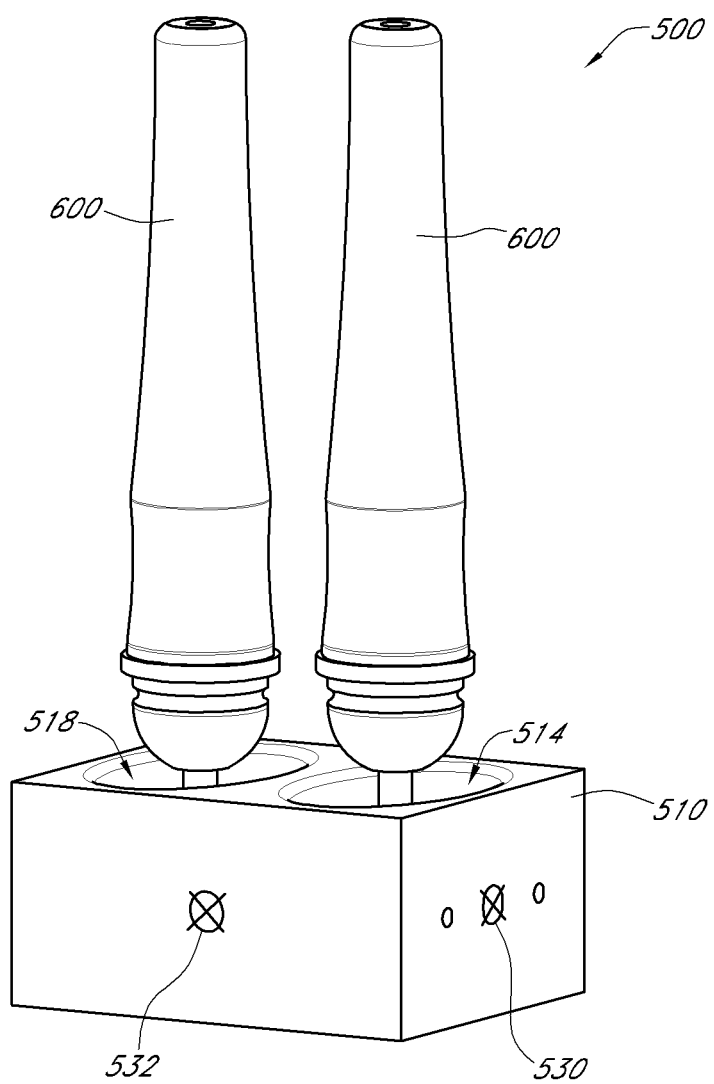
FIGS. 7A and 7B illustrate a station for a skin thermal conditioning system according to one embodiment.
Figure 7B:
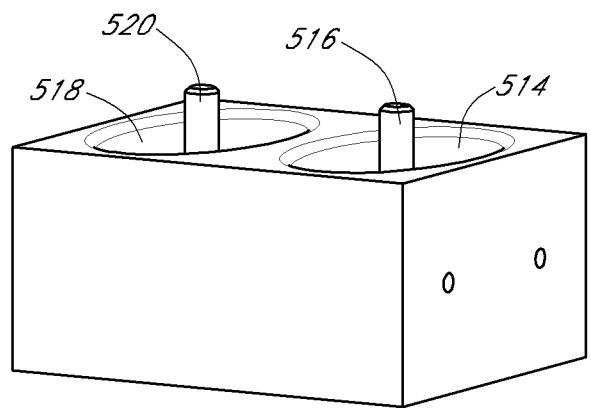

In some embodiments, one or more devices (e.g., handheld devices) can be used to conductively cool and/or heat skin, before, during and/or after a skin treatment procedure (e.g., microdermabrasion). One embodiment of such a heating and cooling system is illustrated in FIGS. 7A and 7B. As shown, the system can include a thermal docking station 510. In some embodiments, the docking station 510 comprises one or more wells, ports or openings 514, 518 for receiving and thermally recharging thermal conditioning handheld assemblies 600.

With continued reference to FIGS. 7A and 7B, the thermal recharging station 510 can be in thermal communication with one or more heating and/or cooling devices (not shown). In some embodiments, one or more thermoelectric devices (e.g., Peltier devices) are positioned along the outside, the inside and/or within the walls of the station 510. However, any other type of heating and/or cooling device can be used. In some embodiments, thermal conditioning devices are positioned along the exterior surfaces of the docking station walls (e.g., as schematically represented by circles 530, 532 in FIG. 7A). Regardless of the quantity, type, location, spacing, orientation and/or configuration of the thermal conditioning devices, the devices can be adapted to conductively heat or cool adjacent portions of the station 510, including the wells 514, 518 that receive the thermal handpiece assemblies 600.

In some embodiments, the station comprises one or more thermally conductive materials, such as, for example, aluminum, copper, other metal or alloys. As illustrated in FIG. 7B, one or more of the wells 514, 518 can include a pin, rod or other protruding member 516, 520. As discussed in greater detail below, the thermal conditioning handheld assemblies 600 can include a central opening. In some embodiments, the assemblies 600 are generally hollow along their centerlines. Accordingly, the assemblies 600 can be conveniently mounted or otherwise positioned on the pins 516, 520 when being placed within the wells 514, 518 of the station 510. Therefore, as illustrated in FIG. 7A, the pins 516, 520 can securely maintain the thermal handheld assemblies in a generally vertical orientation when the assemblies are positioned within the station 510 for thermal recharging.

When the thermoelectric devices and/or other heating and/or cooling devices of the station are activated, the wells of the station can be heated or cooled, in accordance with the desired thermal conditioning effect of that station 510. In some embodiments, if thermoelectric devices are used to heat or cool the station 510, an additional station (not shown) can be positioned on the opposite surface of the thermoelectric device so that the additional station also undergoes heating or cooling (e.g., the opposite thermal effect of the main station).

Figure 8A:
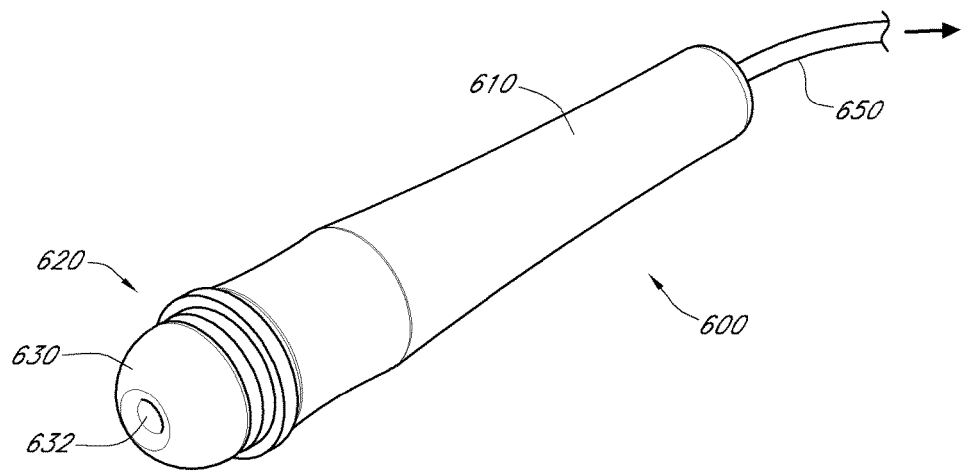
FIGS. 8A and 8B illustrate different views of a thermal conditioning handheld assembly configured for use with the station of FIG. 7A according to one embodiment.
Figure 8B:
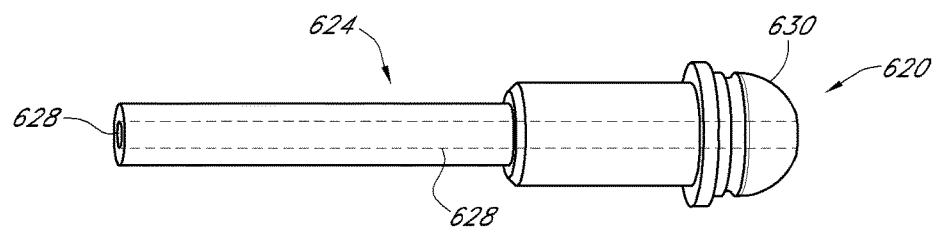

One embodiment of a thermal conditioning handheld assembly 600 is illustrated in FIGS. 8A and 8B. As shown, the assembly 600 can comprise an inner core 620 and an outer housing or shell 610. In some embodiments, the inner core 620 comprises copper and/or any other high heat transfer material (e.g., beryllium). The copper and/or other material can be coated (e.g., plated) with one or more layers of nickel, chrome and/or the like. The outer housing 610 can include ABS, Nylon and/or any other plastic or other material with a relatively low thermal conductivity (e.g., to avoid excessively or uncomfortably hot or cold temperatures being felt by a user who grasps and handles the assembly 600).

As illustrated in FIGS. 8A and 8B and noted above, the thermal handheld assembly 600 can include an interior lumen or opening 628 that extends completely or partially through the assembly. The proximal end of the assembly 600 can be placed in fluid communication with a vacuum conduit 650, if the assembly will be configured for suction. In such arrangements, the conduit 650 is placed in fluid communication with a vacuum or negative pressure source. In some embodiments, however, the heating or cooling system is configured to be used without suction.

With continued reference to FIGS. 8A and 8B, handheld assembly 600 can comprise a distal head 630. In the illustrated embodiment, the head 630 comprises a circular or rounded outer shape, having a generally smooth surface. In some embodiments, the head comprises one or more openings 632 that are in fluid communication with the internal lumen or passage 628 of the assembly 600. As best illustrated in FIG. 8B, in some embodiments, the head 630 forms a unitary structure with and is part of the core 620 of the assembly 600. As such, it advantageously comprises one or more high heat transfer materials (e.g., copper) that can be heated or cooled relatively quickly when placed within a well of the station 510.

Figure 8C:
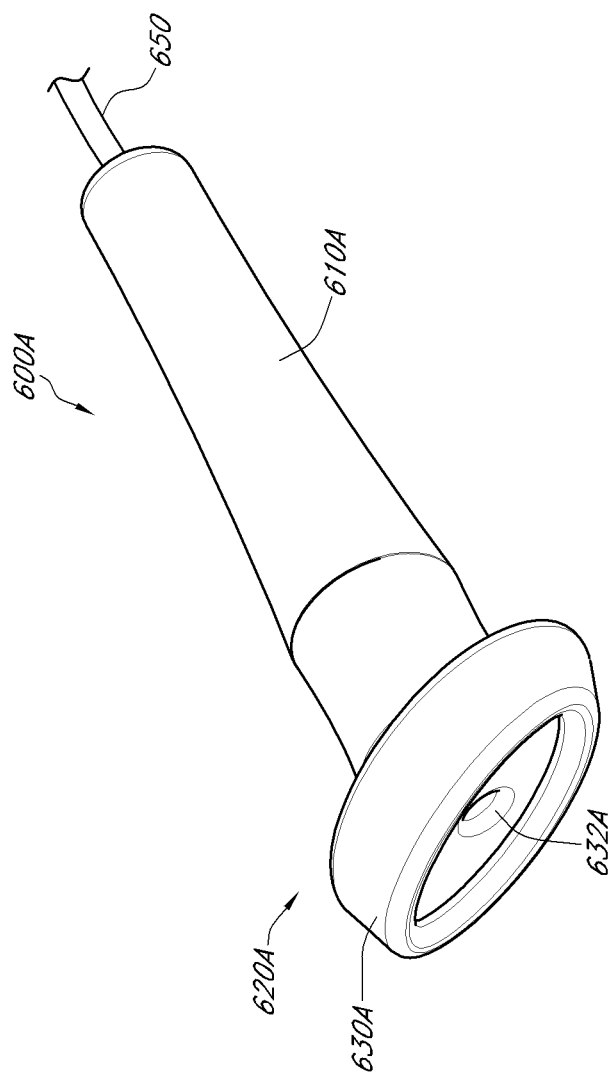
FIG. 8C illustrates a thermal conditioning handheld assembly configured for use with the station of FIG. 7A according to another embodiment.

Another embodiment of a thermal handheld assembly is illustrated in FIG. 8C. As shown, the head 630A of this alternative embodiment is relatively larger than the one illustrated in FIG. 8A. Further, the head 630A is asymmetrical.

Regardless of their exact shape, size, configuration and/or other properties, the thermal handheld assemblies 600, 600A can be used to selectively heat or cool a subject's skin surface. As noted above, in one embodiment, the surface to be abraded (e.g., using microdermabrasion) can first be heated to open the skin pores and/or provide one or more other benefits. With the pores open, a microdermabrasion process can be performed. Accordingly, any serums, other treatment fluids and/or other substances that are delivered to the working end of the microdermabrasion device (e.g., along the skin surface that was previously heated, for example), could pass deeper and/or with greater ease into the open pores of the skin. Following the microdermabrasion process, the user can use a cold thermal conditioning assembly 600, 600A to cool the skin surface that was treated. As a result of cooling the skin surface, the pores of the skin can at least partially close, thereby trapping the potentially beneficial serums and/or other components within the skin. Such a treatment method can provide for a quicker recovery time, fewer complications and/or one or more other benefits or advantages.

As noted above, in some embodiments, the thermal conditioning handheld assemblies 600, 600A are configured to create a negative pressure or vacuum along the one or more openings 632, 632A at the assembly head 630, 630A. As illustrated in FIG. 8B, such openings 632 can be placed in fluid communication with an inner lumen or passage 628 of the core 620, which in turn, is in fluid communication with a vacuum conduit 650. Thus, the vacuum source can be activated in order to draw the subject's body toward, and potentially partially into the opening 632, when the vacuum is activated. Accordingly, the vacuum feature allows a user to maintain the distal head 630 of the assembly 600 in constant or substantially constant contact with the subject's skin during use. In some embodiments, the vacuum source is pulsed (e.g., using a square wave scheme), creating a pulsing effect at the head 630 of the assembly. In some embodiments, the pulsing can be helpful when the thermal conditioning handheld assembly 600, 600A is used to heat or cool sensitive portions of the subject's anatomy (e.g., lymph-rich tissues). In some embodiments, assemblies 600A having larger head (e.g., FIG. 8C) can be used to heat or cool larger portions of the body (e.g., back, torso, thighs, etc.).

According to some embodiments, the level of heating or cooling of the thermal assemblies 600 can be adjusted and controlled (e.g., by modifying the duty cycle of the thermoelectric devices or any other heating or cooling device that is thermally conditioning the station 510). In some embodiments, a thermostat and/or other temperature detection is used to ensure that the operating temperature of the station 510 and the handheld assemblies that the station is configured to heat do not reach dangerous or uncomfortable extremes.

In other embodiments, a skin surface can be heated or cooled using any other method or device. For example, skin can be heated using any of the energy or other modalities discussed herein (e.g., RF, ultrasound, microwave, etc.). In one embodiment, the liquids, serums and/or other treatment fluids delivered to the tip of a microdermabrasion device (e.g., from a vial or cartridge, a bottle of a manifold or tower system, etc.) can be heated or cooled before it reaches the skin surface. Therefore, one or more heating or cooling devices can be incorporated into the microdermabrasion handheld device or the fluid system that is coupled to the handheld device.

F. Manifold System

Figure 9:
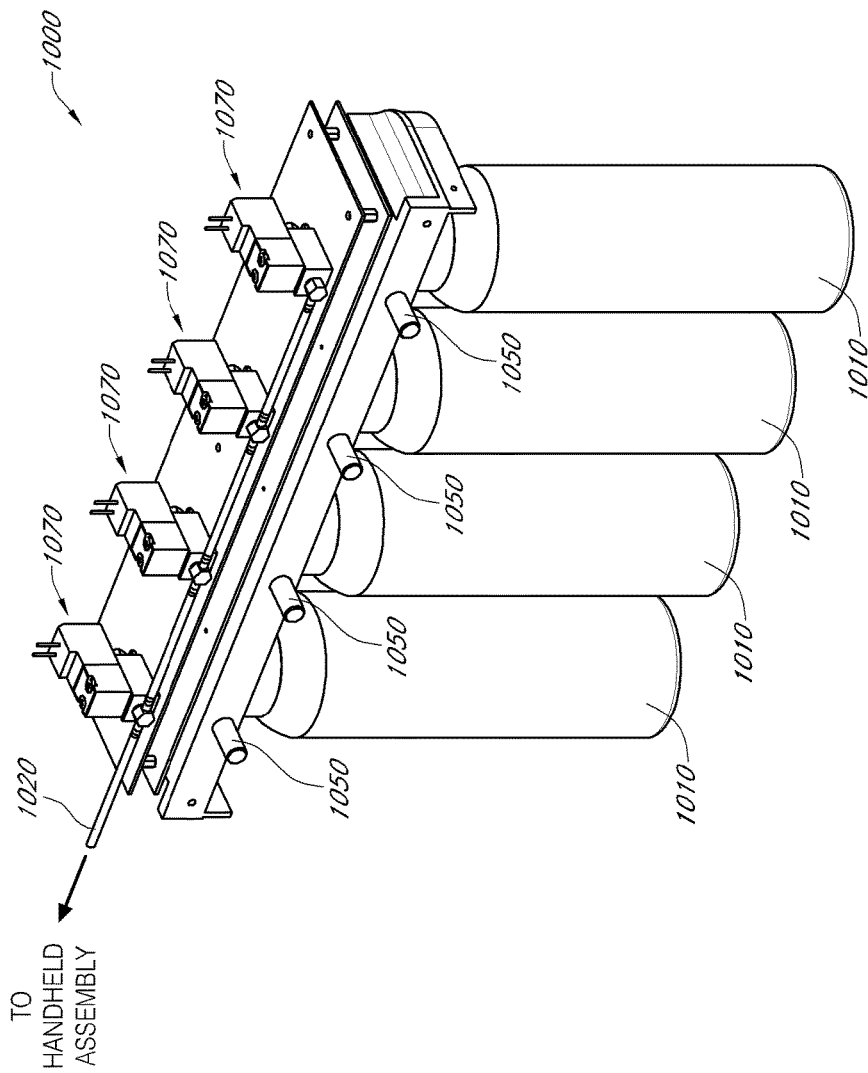
FIG. 9 illustrates a perspective view of one embodiment of a manifold system configured for use in a skin treatment system.

According to some embodiments, as discussed above with reference to the schematic of FIG. 3, a handheld assembly can be in fluid communication with a fluid manifold system (e.g., as opposed to having a vial or other fluid container positioned directly into the handheld assembly). One embodiment of a manifold assembly 1000 configured to receive multiple bottles or containers 1010 of one or more treatment fluids is illustrated in FIG. 9. As shown, the manifold assembly 1000 can include 4 different loading areas, each of which is configured to receive a bottle or other container 1010. Once properly secured to the station, a bottle 1010 can be placed in fluid communication with a main discharge conduit 1020 (e.g., via one or more intermediate conduits, not shown in FIG. 9).

With continued reference to FIG. 9, the manifold system can include a switch 1050 at each station. Therefore, once a bottle 1010 can be properly secured to a station, the corresponding switch can be pressed or otherwise manipulated to activate that station. Accordingly, fluid from the activated container can be used, and the system can deliver a desired volume or amount of that particular liquid to the handpiece assembly during a skin treatment procedure.

With continued reference to FIG. 9, each station of the manifold system 1000 can include a solenoid valve or other flow regulating device 1070 that selectively opens or closes to permit fluid from the corresponding bottle or container 1010 from passing to the main discharge conduit 1020.

Figure 10:
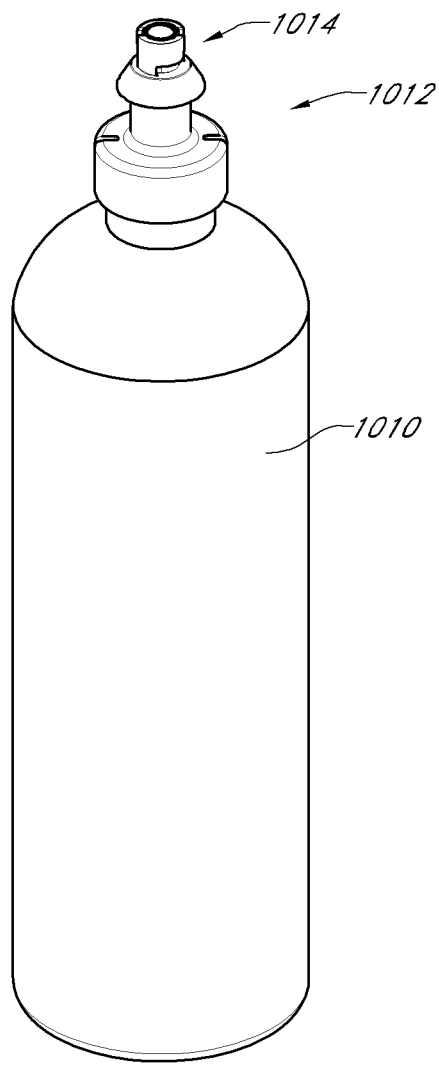
FIG. 10 illustrates a perspective view of one embodiment of a bottle configured for placement within the manifold system of FIG. 9.
Figure 11:
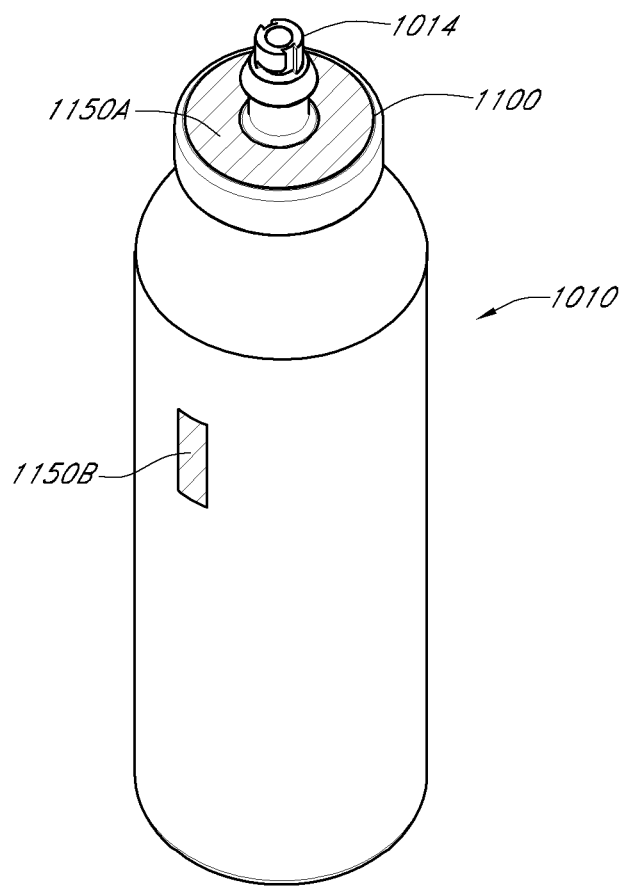
FIG. 11 illustrates the bottle of FIG. 10 comprising automatic identifiers according to one embodiment.
Figure 12:
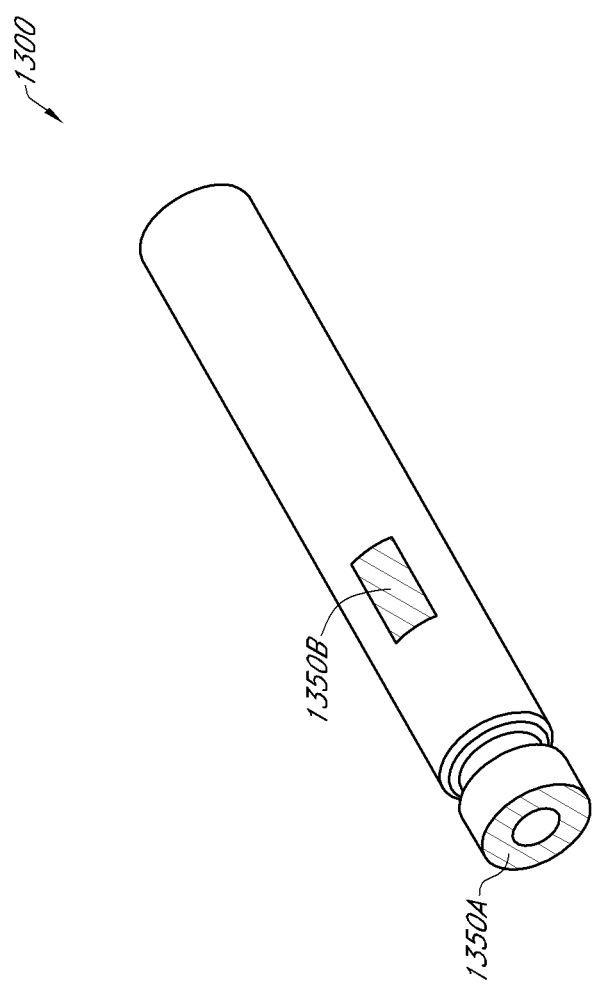
FIG. 12 illustrates a vial configured for placement within a handheld assembly of a skin treatment system according to one embodiment.

One embodiment of a bottle 1010 configured for placement into the manifold system 1000 is illustrated in FIGS. 10 and 11. As shown, the upper end 1012 of the bottle 1010 can include a nozzle fitting 1014 that is shaped, sized and otherwise configured to secure to a corresponding coupling of the manifold system 1000.

G. RFID and Other Identification Features for the Fluid Containers

In some embodiments, the various bottles or other containers 1010 positioned within a manifold system 1000 and/or vials or cartridges 1300 positioned within a recess of the handheld assembly can comprise an automatic identification tag 1150A, 1150B, 1350A, 1350B, such as, for example, a RFID chip, a barcode, etc. Such tags can be used to advantageously store information regarding the specific bottle, vial or other container. For example, the tag can include information regarding the contents of the container, expiration date, manufacturing date, size, lot number, skin procedure with which the contents are intended to be used, other limitations or restrictions on use (e.g., counter-indications, adverse effects, other fluids with which the contents should not be combined, etc.).

The RFID chip or other identifier can be read or otherwise detected (e.g., automatically, manually, etc.) by one or more readers or detectors of a manifold system 1000, a handheld assembly 100 and/or any other portion of a skin treatment system. For example, in some embodiments, such a reader can be placed at or near each station of a manifold system 1000 (e.g., adjacent the portion of the manifold to which the nozzle 1014 of the bottle 1010 secures). Accordingly, the RFID or other type of reader can detect and identify the RFID chip or other identifier of the bottle or other container. Likewise, a RFID or other type of reader can detect and identify the RFID chip or other identifier 1350 of a vial 1300 when the vial 1300 is properly positioned within the handheld assembly.

Therefore, in circumstances where the detected identifier is inconsistent with the proper, safe, appropriate and/or approved operation of the system, the system can be configured to prevent fluid from that vial or container from being used (e.g., by terminating the vacuum source, by maintaining a solenoid valve or other valve in the closed position, etc.).

The use of the RFID chips or other identifiers on the bottles, vials and/or other containers of the system can provide one or more other advantages or benefits. The collection of data regarding use of the corresponding container (e.g., bottle, vial, etc.) can be collected to generate reports for billing, reordering and/or other purposes. In some embodiments, the number of times that a container can be removed and reinserted within a manifold or handheld assembly can be limited (e.g., 1, 2, 3, 4, etc.), as desired or required. For example, such limits can help prevent or reduce the likelihood of contamination of the fluid. In some embodiments, the automatic identification of the fluid container being secured to the system (e.g., manifold station, handheld assembly, etc.) can allow the system to determine if a rinse, flush and/or other preparatory steps are required before the fluid from that container can be used.

The systems, apparatuses, devices and/or other articles disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

What is claimed is:

1. A method of treating a skin surface of a subject, the method comprising:
positioning a distal end of a handpiece assembly along a skin surface of a subject, wherein the distal end comprises a first region and a second region, wherein the first region is fluidly separated and fluidly isolated from the second region by a lip, ridge or other separation member when the distal end of the handpiece assembly is positioned against the skin surface of the subject;

activating a vacuum source to create suction within the first region, wherein the vacuum source is in fluid communication with at least one vacuum port located along the first region;

delivering a fluid to the first region via at least one fluid delivery passage, wherein delivering the fluid to the first region results from the suction created along the first region by activation of the vacuum source when the distal end of the handpiece assembly is positioned against the skin surface; and delivering air to the second region defined by the first region via an air delivery passage;

wherein delivering air to the second region facilitates the transfer of fluid at least partially into the skin.

2. The method of claim 1, wherein air is delivered to the second region in a pulsed manner.

3. The method of claim 1, further comprising at least partially abrading skin tissue using at least one abrasive structure positioned within or along the first region, wherein at least partially abrading skin tissue occurs by moving the handpiece assembly relative to the skin surface when the distal end of the handpiece assembly is positioned along the skin surface and then the vacuum source is activated.

4. The method of claim 3, wherein the at least one abrasive structure in the first region comprises at least one of a protruding member and an abrasive surface.

5. The method of claim 4, wherein the at least protruding member comprises at least one of a spiral ridge and a plurality of posts.

6. The method of claim 3, wherein the at least one abrasive structure comprises at least one of an abrasive disc, a foam pad with an abrasive surface and an abrasive surface.

7. The method of claim 1, wherein at least one product or material is impregnated, embedded, saturated with or otherwise positioned along the distal end of the handpiece assembly, wherein the at least one product or material is configured to be at least partially dissolved or otherwise released when contacted by a solute.

8. A system of treating a skin surface of a subject, the system comprising:

a handpiece assembly comprising a distal end configured to contact a skin surface of a subject, wherein the distal end comprises a first region and a second region, wherein the first region is fluidly separated and fluidly isolated from the second region by a lip, ridge or other separation member when the distal end of the handpiece assembly is positioned against the skin surface of the subject;

at least one vacuum port located along the first region, wherein the at least one vacuum port is configured to be placed in fluid communication with a vacuum source to create suction within the first region;

at least one fluid delivery passage, wherein the at least one fluid delivery passage is configured to be placed in fluid communication with a fluid source, wherein fluid from the fluid source is configured to be delivered to the first region when suction is created along the first region by activation of the vacuum source; and an air delivery passage, wherein air is configured to be delivered to the second region defined by the first region via the air delivery passage;

wherein delivering air to the second region facilitates the transfer of fluid at least partially into the skin.

9. The system of claim 8, wherein air is delivered to the second region in a pulsed manner.

10. The system of claim 8, further comprising at least one abrasive structure positioned within or along the first region.

11. The system of claim 10, wherein the at least one abrasive structure in the first region comprises at least one of a protruding member and an abrasive surface.

12. The system of claim 11, wherein the at least protruding member comprises at least one of a spiral ridge and a plurality of posts.

13. The system of claim 10, wherein the at least one abrasive structure comprises at least one of an abrasive disc, a foam pad with an abrasive surface and an abrasive surface.

14. The system of claim 8, further comprising at least one product or material impregnated, embedded, saturated with or otherwise positioned along the distal end of the handpiece assembly, wherein the at least one product or material is configured to be at least partially dissolved or otherwise released when contacted by a solute.

* * * * *